US010512471B2

(12) United States Patent
nguyen et al.

(10) Patent No.: US 10,512,471 B2
(45) Date of Patent: Dec. 24, 2019

(54) KNEE ARTHROPLASTY SYSTEMS AND METHODS

(71) Applicant: Optimotion Implants LLC, Orlando, FL (US)

(72) Inventors: Vuong binh nguyen, Windermere, FL (US); Daniel F. Justin, Orlando, FL (US); Dinesh V. Koka, Winter Park, FL (US)

(73) Assignee: Optimotion Implants LLC, Orlando, FL (US)

( * ) Notice: Subject to any disclaimer, the term of this patent is extended or adjusted under 35 U.S.C. 154(b) by 328 days.

(21) Appl. No.: 15/624,488

(22) Filed: Jun. 15, 2017

(65) Prior Publication Data

US 2018/0250022 A1 Sep. 6, 2018

Related U.S. Application Data

(60) Provisional application No. 62/466,249, filed on Mar. 2, 2017.

(51) Int. Cl.
*A61B 17/58* (2006.01)
*A61B 17/60* (2006.01)
(Continued)

(52) U.S. Cl.
CPC .......... *A61B 17/154* (2013.01); *A61B 17/142* (2016.11); *A61B 17/155* (2013.01); *A61B 17/157* (2013.01); *A61B 17/1675* (2013.01); *A61B 17/1764* (2013.01); *A61F 2/30767* (2013.01); *A61F 2/30771* (2013.01);
(Continued)

(58) Field of Classification Search
CPC combination set(s) only.
See application file for complete search history.

(56) References Cited

U.S. PATENT DOCUMENTS 5,653,714 A 8/1997 Dietz et al.
5,658,334 A 8/1997 Caldarise et al.
(Continued)

FOREIGN PATENT DOCUMENTS

AU 2003261497 B2 5/2004
AU 2004204267 B2 7/2004
(Continued)

OTHER PUBLICATIONS

Rapid Solid-State Synthesis of Titanium Aluminides, Richard G. Blair, Jan. 9, 2003.
(Continued)

*Primary Examiner* — Sameh R Boles
(74) *Attorney, Agent, or Firm* — David Meibos; Maywood IP Law

(57) ABSTRACT

A knee arthroplasty system may have a femoral joint prosthesis with a femoral bone engagement surface with an anterior portion, a posterior portion, and a distal portion that connects the anterior portion to the posterior portion. A first femoral anchoring member may protrude from the distal portion, and may be connected to the anterior portion with a primary femoral web. A tibial resection guide may have a base member and a guide member with a slot that guides a cutting blade to resect the tibial plateau. The guide member may slide along an arcuate path relative to the base member.

20 Claims, 19 Drawing Sheets

(51) Int. Cl.
*A61F 2/00* (2006.01)
*A61B 17/15* (2006.01)
*A61B 17/17* (2006.01)
*A61F 2/38* (2006.01)
*A61B 17/14* (2006.01)
*A61B 17/16* (2006.01)
*A61F 2/46* (2006.01)
*A61F 2/30* (2006.01)
*B33Y 10/00* (2015.01)
*B33Y 80/00* (2015.01)
*B22F 3/105* (2006.01)
*B22F 7/08* (2006.01)
*B22F 3/11* (2006.01)
*B22F 7/06* (2006.01)

(52) U.S. Cl.
CPC ............... *A61F 2/38* (2013.01); *A61F 2/389* (2013.01); *A61F 2/3859* (2013.01); *A61F 2/461* (2013.01); *A61F 2/30744* (2013.01); *A61F 2002/305* (2013.01); *A61F 2002/30011* (2013.01); *A61F 2002/3038* (2013.01); *A61F 2002/3084* (2013.01); *A61F 2002/3092* (2013.01); *A61F 2002/3093* (2013.01); *A61F 2002/3097* (2013.01); *A61F 2002/30332* (2013.01); *A61F 2002/30448* (2013.01); *A61F 2002/30451* (2013.01); *A61F 2002/30604* (2013.01); *A61F 2002/30818* (2013.01); *A61F 2002/30841* (2013.01); *A61F 2002/30845* (2013.01); *A61F 2002/30878* (2013.01); *A61F 2002/30884* (2013.01); *A61F 2002/30968* (2013.01); *A61F 2002/30985* (2013.01); *A61F 2310/00023* (2013.01); *A61F 2310/00029* (2013.01); *A61F 2310/00059* (2013.01); *A61F 2310/00383* (2013.01); *B22F 3/1055* (2013.01); *B22F 3/11* (2013.01); *B22F 7/062* (2013.01); *B22F 7/08* (2013.01); *B22F 2207/17* (2013.01); *B22F 2998/10* (2013.01); *B22F 2999/00* (2013.01); *B33Y 10/00* (2014.12); *B33Y 80/00* (2014.12); *Y02P 10/295* (2015.11)

(56) References Cited

U.S. PATENT DOCUMENTS

| | | |
|---|---|---|
| 5,658,341 A | 8/1997 | Delfosse |
| 5,687,788 A | 11/1997 | Caldarise et al. |
| 5,716,412 A | 2/1998 | DeCarlo, Jr. et al. |
| 5,762,125 A | 6/1998 | Mastrorio |
| 5,824,100 A | 10/1998 | Kester et al. |
| 5,824,103 A | 10/1998 | Williams |
| 5,897,592 A | 4/1999 | Caldarise et al. |
| 5,910,173 A | 6/1999 | DeCarlo, Jr. et al. |
| 5,980,974 A | 11/1999 | Armini et al. |
| 6,087,553 A | 7/2000 | Cohen et al. |
| 6,105,235 A | 8/2000 | Caldarise |
| 6,165,221 A | 12/2000 | Schmotzer |
| RE37,277 E | 7/2001 | Baldwin et al. |
| 6,258,127 B1 | 7/2001 | Schmotzer |
| 6,506,216 B1 | 1/2003 | McCue et al. |
| 6,652,588 B2 | 11/2003 | Hayes, Jr. et al. |
| 6,858,032 B2 | 2/2005 | Chow et al. |
| 6,945,448 B2 | 9/2005 | Medlin et al. |
| 6,974,625 B2 | 12/2005 | Hunter et al. |
| 7,001,672 B2 | 2/2006 | Justin et al. |
| 7,081,137 B1 | 7/2006 | Servidio |
| 7,087,200 B2 | 8/2006 | Taboas et al. |
| 7,105,030 B2 | 9/2006 | Despres, III et al. |
| 7,160,330 B2 | 1/2007 | Axelson, Jr. et al. |
| 7,182,786 B2 | 2/2007 | Justin et al. |
| 7,189,262 B2 | 3/2007 | Hayes, Jr. et al. |
| 7,258,810 B2 | 8/2007 | Hunter et al. |
| 7,294,149 B2 | 11/2007 | Hozack et al. |
| 7,309,339 B2 | 12/2007 | Cusick et al. |
| 7,357,817 B2 | 4/2008 | D'Alessio, II |
| 7,413,577 B1 | 8/2008 | Servidio |
| 7,445,640 B2 | 11/2008 | Despres, III et al. |
| 7,497,874 B1 | 3/2009 | Metzger et al. |
| 7,513,912 B2 | 4/2009 | Hayes, Jr. et al. |
| 7,524,334 B2 | 4/2009 | Haidukewych |
| 7,537,664 B2 | 5/2009 | O'Neil et al. |
| 7,578,851 B2 | 8/2009 | Dong et al. |
| 7,625,407 B2 | 12/2009 | Akizuki et al. |
| 7,628,817 B1 | 12/2009 | Axelson, Jr. et al. |
| 7,632,575 B2 | 12/2009 | Justin et al. |
| 7,648,735 B2 | 1/2010 | Hunter et al. |
| 7,666,522 B2 | 2/2010 | Justin et al. |
| 7,771,484 B2 | 8/2010 | Campbell |
| 7,837,690 B2 | 11/2010 | Metzger |
| 7,850,862 B2 | 12/2010 | Amrich et al. |
| 7,857,858 B2 | 12/2010 | Justin et al. |
| 7,887,542 B2 | 2/2011 | Metzger et al. |
| 7,918,382 B2 | 4/2011 | Charlebois et al. |
| 7,938,833 B2 | 5/2011 | Bastian |
| 8,070,821 B2 | 12/2011 | Roger |
| 8,075,628 B2 | 12/2011 | Justin et al. |
| 8,142,886 B2 | 3/2012 | Noble et al. |
| 8,147,861 B2 | 4/2012 | Jones et al. |
| 8,162,949 B2 | 4/2012 | Duggineni et al. |
| 8,167,954 B2 | 5/2012 | Despres, III et al. |
| 8,191,760 B2 | 6/2012 | Charlebois et al. |
| 8,241,367 B2 | 8/2012 | Justin et al. |
| 8,268,099 B2 | 9/2012 | O'Neill et al. |
| 8,268,100 B2 | 9/2012 | O'Neill et al. |
| 8,350,186 B2 | 1/2013 | Jones et al. |
| 8,357,201 B2 | 1/2013 | Mayer et al. |
| 8,388,887 B2 | 3/2013 | Gupta et al. |
| 8,414,908 B2 | 4/2013 | Sungho et al. |
| 8,518,047 B2 | 8/2013 | Metzger et al. |
| 8,551,100 B2 | 10/2013 | Metzger |
| 8,556,981 B2 | 10/2013 | Jones et al. |
| 8,632,600 B2 | 1/2014 | Zannis et al. |
| 8,663,337 B2 | 3/2014 | Anderson et al. |
| 8,715,359 B2 | 5/2014 | Deffenbaugh et al. |
| 8,728,387 B2 | 5/2014 | Jones et al. |
| 8,735,773 B2 | 5/2014 | Lang |
| 8,758,444 B2 | 6/2014 | Wentorf et al. |
| 8,790,345 B2 | 7/2014 | Anderson |
| 8,843,229 B2 | 9/2014 | Vanasse et al. |
| 8,870,883 B2 | 10/2014 | Metzger et al. |
| 8,900,316 B2 | 12/2014 | Lenz et al. |
| 8,900,317 B2 | 12/2014 | Zubok et al. |
| 8,951,465 B2 | 2/2015 | Gupta |
| 8,985,430 B2 | 3/2015 | Charlebois et al. |
| 8,992,703 B2 | 3/2015 | O'Neill et al. |
| 9,023,053 B2 | 5/2015 | Metzger |
| 9,072,605 B2 | 7/2015 | Coon et al. |
| 9,161,761 B2 | 10/2015 | Metzger et al. |
| 9,192,459 B2 | 11/2015 | Bonutti |
| 9,226,827 B2 | 1/2016 | Luscher |
| 9,237,950 B2 | 1/2016 | Hensley et al. |
| 9,265,613 B2 | 2/2016 | Nevins et al. |
| 9,278,003 B2 | 3/2016 | Deffenbaugh et al. |
| 9,289,301 B2 | 3/2016 | Mayer et al. |
| 9,301,846 B2 | 4/2016 | Landon |
| 9,370,605 B2 | 6/2016 | Zhang et al. |
| 9,381,085 B2 | 7/2016 | Axelson, Jr. et al. |
| 9,427,334 B2 | 8/2016 | Axelson, Jr. et al. |
| 9,445,823 B2 | 9/2016 | Harris et al. |
| 9,445,902 B2 | 9/2016 | Klein et al. |
| 9,445,909 B2 | 9/2016 | Cohen et al. |
| 9,452,051 B2 | 9/2016 | Collazo et al. |
| 9,456,901 B2 | 10/2016 | Jones et al. |
| 9,480,511 B2 | 11/2016 | Butters et al. |
| 9,517,134 B2 | 12/2016 | Lang |
| 9,517,138 B2 | 12/2016 | Zubok et al. |
| 9,554,862 B2 | 1/2017 | Davignon et al. |
| 9,636,229 B2 | 5/2017 | Lang et al. |
| 9,649,195 B2 | 5/2017 | Bechtold et al. |

(56) References Cited

U.S. PATENT DOCUMENTS

| | | |
|---|---|---|
| 9,655,632 B2 | 5/2017 | Dmuschewsky et al. |
| 9,656,358 B2 | 5/2017 | Charlebois et al. |
| 9,662,214 B2 | 5/2017 | Li et al. |
| 9,668,863 B2 | 6/2017 | Sharp et al. |
| 9,668,871 B2 | 6/2017 | Irwin et al. |
| 2008/0215157 A1 | 9/2008 | Earl et al. |
| 2010/0016987 A1 | 1/2010 | Scrafton et al. |
| 2010/0318089 A1 | 12/2010 | Metzger et al. |
| 2011/0029093 A1 | 2/2011 | Bojarski et al. |
| 2013/0218288 A1 | 8/2013 | Fonte et al. |
| 2014/0010951 A1 | 1/2014 | Vargas et al. |
| 2014/0257504 A1 | 9/2014 | Dong et al. |
| 2014/0257507 A1 | 9/2014 | Wang et al. |
| 2014/0277540 A1 | 9/2014 | Leszko |
| 2014/0316528 A1 | 10/2014 | Bechtold et al. |
| 2014/0371863 A1 | 12/2014 | Vanasse et al. |
| 2015/0032218 A1 | 1/2015 | Landon |
| 2015/0093283 A1 | 4/2015 | Miller et al. |
| 2015/0305754 A1 | 10/2015 | Metzger |
| 2015/0305878 A1 | 10/2015 | O'Neil et al. |
| 2015/0342742 A1 | 12/2015 | Ferro et al. |
| 2015/0359638 A1 | 12/2015 | Khowaylo et al. |
| 2016/0157906 A1 | 6/2016 | Hollis et al. |
| 2016/0157908 A1 | 6/2016 | Cawley et al. |
| 2016/0199193 A1 | 7/2016 | Willis et al. |
| 2016/0213821 A1 | 7/2016 | Melkent et al. |
| 2016/0228255 A1 | 8/2016 | Samuelson et al. |
| 2016/0278929 A1 | 9/2016 | Harris et al. |
| 2016/0296289 A1 | 10/2016 | Choudhury et al. |
| 2016/0310279 A1 | 10/2016 | Samuelson et al. |
| 2016/0374814 A1 | 12/2016 | Collazo et al. |
| 2017/0027700 A1 | 2/2017 | Cohen et al. |
| 2017/0042576 A1 | 2/2017 | Butters et al. |
| 2017/0056025 A1 | 3/2017 | Trachsler et al. |
| 2017/0071744 A1 | 3/2017 | Bali et al. |
| 2018/0250022 A1* | 9/2018 | nguyen .............. A61B 17/1675 |

FOREIGN PATENT DOCUMENTS

| | | |
|---|---|---|
| AU | 2006252296 B2 | 7/2007 |
| AU | 2009212243 B2 | 8/2009 |
| AU | 2009270566 B2 | 1/2017 |
| CA | 2448592 C | 5/2004 |
| CA | 2859970 A1 | 7/2013 |
| CA | 2844788 C | 9/2014 |
| EP | 1418013 B1 | 1/2005 |
| EP | 1683593 A2 | 7/2006 |
| EP | 1911468 B1 | 9/2009 |
| EP | 2210623 A1 | 7/2010 |
| EP | 1800700 B1 | 9/2010 |
| EP | 1398045 B1 | 6/2012 |
| EP | 2467097 A1 | 6/2012 |
| EP | 2709564 A1 | 3/2014 |
| EP | 2797557 A1 | 11/2014 |
| EP | 2797558 A1 | 11/2014 |
| EP | 2485778 B1 | 8/2015 |
| EP | 2685938 B1 | 8/2015 |
| EP | 2774580 B1 | 10/2016 |
| EP | 2967885 B1 | 12/2016 |
| EP | 2651341 B1 | 1/2017 |
| EP | 2874570 B1 | 1/2017 |
| EP | 3127510 A1 | 2/2017 |
| EP | 1803513 B1 | 3/2017 |
| EP | 2949293 B1 | 3/2017 |
| EP | 3178448 A1 | 6/2017 |
| GB | 2388034 B | 11/2013 |
| WO | WO2016010895 A1 | 1/2016 |

OTHER PUBLICATIONS

Size Controlled Mechochemical Synthesis of ZrSi2, David Restrepo, Aug. 30, 2012.
Bone Ingrowth Performance of OsteoSync Ti, Document: 2007-001-40 Rev A.
Mechanical Characteristics of OsteoSync Ti, Document: 2007-001-41 Rev A.
International Search Report and Written Opinion dated May 31, 2018 for corresponding PCT Application No. PCT/US2018/019652.

* cited by examiner

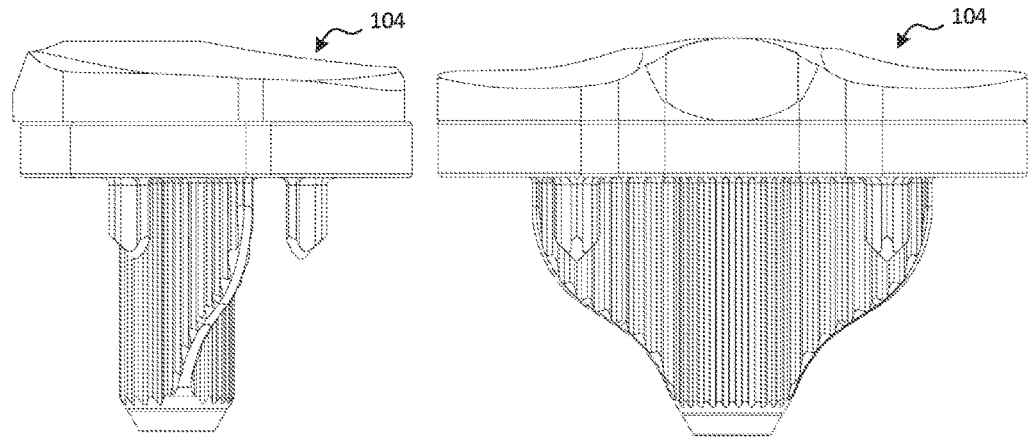
*Fig. 5A*  *Fig. 5B*
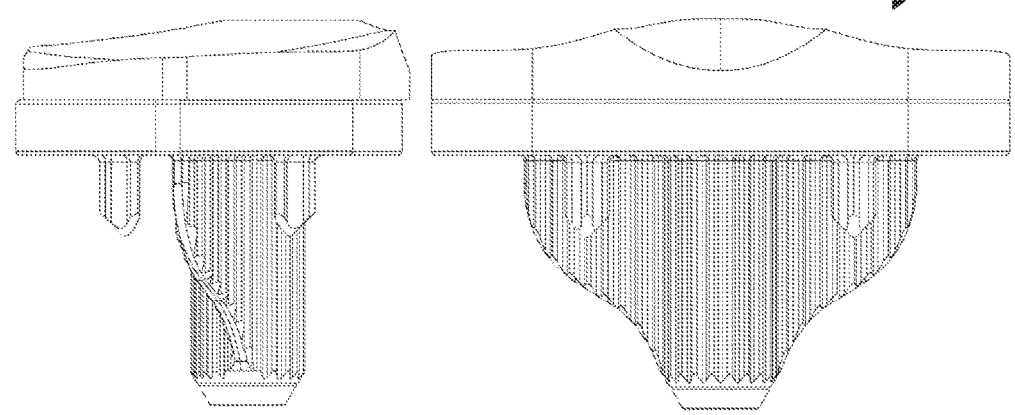
*Fig. 5C*  *Fig. 5D*
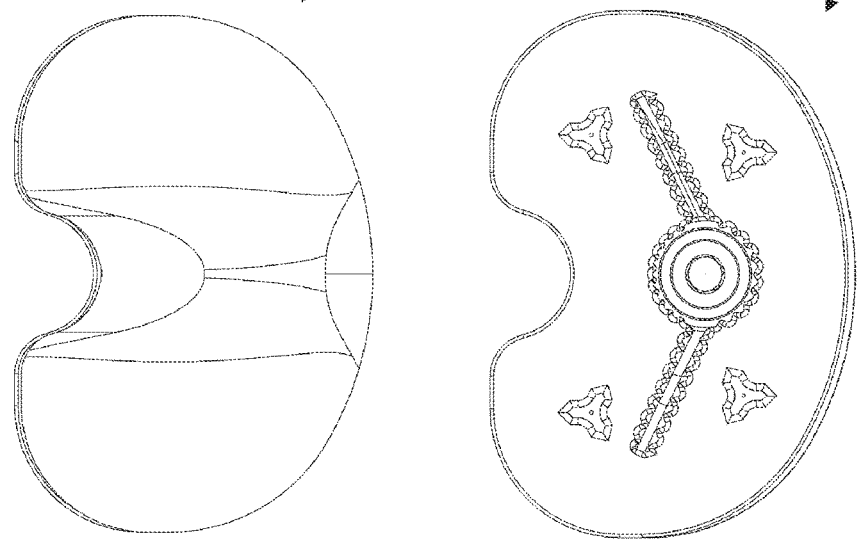
*Fig. 5E*  *Fig. 5F*

KNEE ARTHROPLASTY SYSTEMS AND METHODS

RELATED APPLICATIONS

The present application claims the benefit of U.S. Provisional Application Ser. No. 62/466,249, entitled COMPOSITE JOINT ARTHROPLASTY SYSTEMS AND METHODS, filed Mar. 2, 2017, which is incorporated herein by reference in its entirety.

TECHNICAL FIELD

The present disclosure relates to surgical systems and methods. More specifically, the present disclosure relates to implants and related methods for joint arthroplasty.

BACKGROUND

Joint arthroplasty procedures are surgical procedures in which one or more articulating surfaces of a joint are replaced with prosthetic articulating surfaces. Such procedures are becoming increasingly commonplace, particularly for knees.

For a successful knee arthroplasty, it is important that the knee implants remain in place and maintain the necessary wear characteristics. Further, it is desirable for the knee arthroplasty procedure to be carried out quickly and smoothly. Many existing knee arthroplasty implants and methods are time-consuming to implant, do not form a sufficient attachment to the underlying bone, or leave excessive wear debris.

SUMMARY

The various systems and methods of the present disclosure have been developed in response to the present state of the art, and in particular, in response to the problems and needs in the art that have not yet been fully solved by currently available knee arthroplasty systems and methods. The systems and methods of the present disclosure may provide knee implants and instruments, including but not limited to femoral and tibial prostheses and tibial resection guides, that provide enhanced bone fixation, less wear debris, and/or streamlined implantation.

According to some embodiments, a knee arthroplasty system may be designed to replace a natural femoral articular surface on a femur and a natural tibial articular surface on a tibia. The knee arthroplasty system may have a femoral joint prosthesis with a femoral joint-facing side with a femoral articular surface, and a femoral bone-facing side. The femoral bone-facing side may have a femoral bone engagement surface securable to a resected femoral surface of the femur, a first femoral anchoring member, and a primary femoral web. The femoral bone engagement surface may have an anterior portion, a posterior portion, and a distal portion that connects the anterior portion to the posterior portion. The first femoral anchoring member may protrude from the distal portion. The primary femoral web may connect the first femoral anchoring member to the anterior portion. The knee arthroplasty system may also have a tibial joint prosthesis with a tibial joint-facing side and a tibial bone-facing side. The tibial joint-facing side may have a tibial articular surface positioned such that, with the femoral joint prosthesis secured to the femur and the tibial joint prosthesis secured to the tibia, the tibial articular surface articulates with the femoral articular surface. The tibial bone-facing side may have a tibial bone engagement surface securable to a resected tibial surface of the tibia.

The distal portion may have a distal face, an anterior-distal face, and a posterior-distal face, each of which is substantially planar. The anterior-distal face may extend between the distal face and the anterior portion. The anterior-distal face may be oriented, relative to each of the distal face and the anterior portion, at an obtuse angle greater than 90° and less than 180°. The posterior-distal face may extend between the distal face and the posterior portion. The posterior-distal face may be oriented, relative to each of the distal face and the posterior portion, at an obtuse angle greater than 90° and less than 180°. The femoral bone-facing side may further have a first anchoring post protruding from the distal face, and a second anchoring post protruding from the distal face.

The first femoral anchoring member may protrude from and may be formed as a single piece with the anterior-distal face and the primary femoral web. The first femoral anchoring member may have a beveled tip.

The femoral bone-facing side may further have a second femoral anchoring member protruding from the femoral bone engagement surface, and a first femoral web that connects the first femoral anchoring member to the second femoral anchoring member. The femoral bone-facing side may further have a third femoral anchoring member protruding from the femoral bone engagement surface such that the first femoral anchoring member is directly between the first femoral anchoring member and the second femoral anchoring member, and a second femoral web, coplanar with the first femoral web, that connects the first femoral anchoring member to the third femoral anchoring member. The second femoral anchoring member and the first femoral web may cooperate to define a first bevel extending from a tip of the first femoral anchoring member toward the distal portion. The third femoral anchoring member and the second femoral web may cooperate to define a second bevel extending from the tip of the first femoral anchoring member toward the distal portion.

The tibial bone-facing side may further have a post protruding from the tibial bone engagement surface, a first tibial web that connects the post to the tibial bone engagement surface, the first tibial web comprising crenellated surface, and a second tibial web that connects the post to the tibial bone engagement surface, the second tibial web comprising crenellated surface. The post may have a bore, and the tibial joint prosthesis may further have a keel with a proximal end receivable within the bore, and a distal end configured to protrude beyond the bore when the proximal end is seated within the bore.

The femoral joint-facing side may be a femoral articulating component joint-facing side. The femoral bone-facing side may be a femoral bone anchoring component bone-facing side. The femoral joint prosthesis may further have a femoral articulating component with the femoral articulating component joint-facing side and a femoral articulating component bone-facing side, and a femoral bone anchoring component with the femoral bone anchoring component bone-facing side and a femoral bone anchoring component joint-facing side. The femoral articulating component bone-facing side may be secured to the femoral bone anchoring component joint-facing side.

The tibial joint-facing side may be a tibial articulating component joint-facing side. The tibial bone-facing side may be a tibial bone anchoring component bone-facing side. The tibial joint prosthesis may further have a tibial articulating component with the tibial articulating component joint-facing side and a tibial articulating component bone-facing side, and a tibial bone anchoring component with the tibial bone anchoring component bone-facing side and a tibial bone anchoring component joint-facing side. The tibial articulating component bone-facing side may be secured to the tibial bone anchoring component joint-facing side.

Further, according to some embodiments, a knee arthroplasty system may be designed to replace a natural femoral articular surface on a femur and a natural tibial articular surface on a tibia. The knee arthroplasty system may have a femoral joint prosthesis with a femoral joint-facing side with a femoral articular surface and a femoral bone-facing side with a femoral bone engagement surface securable to a resected femoral surface of the femur, a first femoral anchoring member, a second femoral anchoring member, and a first femoral web. The femoral bone engagement surface may have an anterior portion, a posterior portion, and a distal portion that connects the anterior portion to the posterior portion. The first femoral anchoring member may protrude from the distal portion. The second femoral anchoring member may protrude from the femoral bone engagement surface. The first femoral web may connect the first femoral anchoring member to the second femoral anchoring member. The knee arthroplasty system may further have a tibial joint prosthesis with a tibial joint-facing side with a tibial articular surface positioned such that, with the femoral joint prosthesis secured to the femur and the tibial joint prosthesis secured to the tibia, the tibial articular surface articulates with the femoral articular surface, and a tibial bone-facing side with a tibial bone engagement surface securable to a resected tibial surface of the tibia.

The distal portion may have a distal face, an anterior-distal face, and a posterior-distal face, each of which is substantially planar. The anterior-distal face may extend between the distal face and the anterior portion. The anterior-distal face may be oriented, relative to each of the distal face and the anterior portion, at an obtuse angle greater than 90° and less than 180°. The posterior-distal face may extend between the distal face and the posterior portion. The posterior-distal face may be oriented, relative to each of the distal face and the posterior portion, at an obtuse angle greater than 90° and less than 180°. The femoral bone-facing side may further have a first anchoring post protruding from the distal face, and a second anchoring post protruding from the distal face.

The first femoral anchoring member and the second femoral anchoring member may protrude from and may be formed as a single piece with the anterior-distal face. The first femoral anchoring member may have a beveled tip.

The femoral bone-facing side may further have a third femoral anchoring member protruding from the femoral bone engagement surface such that the first femoral anchoring member is directly between the first femoral anchoring member and the second femoral anchoring member, and a second femoral web, coplanar with the first femoral web, that connects the first femoral anchoring member to the third femoral anchoring member. The second femoral anchoring member and the first femoral web may cooperate to define a first bevel extending from a tip of the first femoral anchoring member toward the distal portion. The third femoral anchoring member and the second femoral web may cooperate to define a second bevel extending from the tip of the first femoral anchoring member toward the distal portion.

The tibial bone-facing side may further have a post protruding from the tibial bone engagement surface, a first tibial web that connects the post to the tibial bone engagement surface, the first tibial web comprising crenellated surface, and a second tibial web that connects the post to the tibial bone engagement surface. The second tibial web may have crenellated surface. The post may have a bore. The tibial joint prosthesis may further have a keel with a proximal end receivable within the bore, and a distal end configured to protrude beyond the bore when the proximal end is seated within the bore.

The femoral joint-facing side may be a femoral articulating component joint-facing side. The femoral bone-facing side may be a femoral bone anchoring component bone-facing side. The femoral joint prosthesis may further have a femoral articulating component with the femoral articulating component joint-facing side and a femoral articulating component bone-facing side, and a femoral bone anchoring component with the femoral bone anchoring component bone-facing side and a femoral bone anchoring component joint-facing side. The femoral articulating component bone-facing side may be secured to the femoral bone anchoring component joint-facing side. The tibial joint-facing side may be a tibial articulating component joint-facing side. The tibial bone-facing side may be a tibial bone anchoring component bone-facing side. The tibial joint prosthesis may further have a tibial articulating component with the tibial articulating component joint-facing side and a tibial articulating component bone-facing side, and a tibial bone anchoring component with the tibial bone anchoring component bone-facing side and a tibial bone anchoring component joint-facing side. The tibial articulating component bone-facing side may be secured to the tibial bone anchoring component joint-facing side.

According to some embodiments, a knee arthroplasty system may be designed to replace a natural femoral articular surface on a femur and a natural tibial articular surface on a tibia. The knee arthroplasty system may have femoral joint prosthesis with a femoral joint-facing side comprising a femoral articular surface, and a femoral bone-facing side with a femoral bone engagement surface securable to a resected femoral surface of the femur, a first femoral anchoring member, a primary femoral web, a second femoral anchoring member, a third femoral anchoring member, a first femoral web, and a second femoral web. The femoral bone engagement surface may have an anterior portion, a posterior portion, and a distal portion that connects the anterior portion to the posterior portion. The first femoral anchoring member may protrude from the distal portion. The primary femoral web may connect the first femoral anchoring member to the anterior portion. The second femoral anchoring member may protrude from the distal portion. The third femoral anchoring member may protrude from the distal portion. The first femoral web may connect the first femoral anchoring member to the second femoral anchoring member. The second femoral web may connect the first femoral anchoring member to the third femoral anchoring member. The knee arthroplasty system may also have a tibial joint prosthesis with a tibial joint-facing side with a tibial articular surface positioned such that, with the femoral joint prosthesis secured to the femur and the tibial joint prosthesis secured to the tibia, the tibial articular surface articulates with the femoral articular surface, and a tibial bone-facing side with a tibial bone engagement surface securable to a resected tibial surface of the tibia.

The femoral joint-facing side may be a femoral articulating component joint-facing side. The femoral bone-facing side may be a femoral bone anchoring component bone-facing side. The femoral joint prosthesis may further have a femoral articulating component with the femoral articulating component joint-facing side and a femoral articulating component bone-facing side, and a femoral bone anchoring component with the femoral bone anchoring component bone-facing side and a femoral bone anchoring component joint-facing side. The femoral articulating component bone-facing side may be secured to the femoral bone anchoring component joint-facing side. The tibial joint-facing side may be a tibial articulating component joint-facing side. The tibial bone-facing side may be a tibial bone anchoring component bone-facing side. The tibial joint prosthesis may further have a tibial articulating component with the tibial articulating component joint-facing side and a tibial articulating component bone-facing side, and a tibial bone anchoring component with the tibial bone anchoring component bone-facing side and a tibial bone anchoring component joint-facing side. The tibial articulating component bone-facing side may be secured to the tibial bone anchoring component joint-facing side.

According to some embodiments, a tibial resection guide may be configured to facilitate resection of a tibia to prepare the tibia for attachment of a tibial prosthesis. The tibial resection guide may have an anchoring assembly that secures the tibial resection guide to the tibia, a base member, a positioning assembly extending between the anchoring assembly and the base member to adjustably position the base member proximate a tibial plateau of the tibia, and a guide member with a slot sized to receive a cutting blade configured to resect the tibial plateau. The guide member may be movably coupled to the base member such that the guide member is movable along an arcuate path, relative to the base member, around the tibial plateau.

The base member may have a base member attachment feature. The guide member may have a guide member attachment feature. The guide member attachment feature may have a shape complementary to that of the base member attachment feature such that the guide member attachment feature and the base member attachment feature cooperate to slidably couple the guide member to the base member. One of the base member attachment feature and the guide member attachment feature may have a dovetail-shaped protrusion extending along a first arcuate pathway. The other of the base member attachment feature and the guide member attachment feature may have a dovetail-shaped recess extending along a second arcuate pathway. The dovetail-shaped recess may slidably receive the dovetail-shaped protrusion.

The base member may have two base member attachment features positioned proximate two opposing ends of the base member. The positioning assembly may be attachable to either of the base member attachment features. The guide member may have a plurality of apertures through which bone pins can be inserted into the tibia to retain the guide member relative to the tibia.

The tibial resection guide may further have a locking member movably coupled to at least one of the base member and the guide member. The locking member may be actuatable between a locked configuration and an unlocked configuration. With the locking member in the locked configuration, the guide member may be fixedly secured to the base member. With the locking member in the unlocked configuration, the guide member may be movable along the arcuate path, relative to the base member.

The locking member may have a plurality of locking posts, each of which has a tip. The base member may have a plurality of locking holes, each of which receives one of the locking posts. The guide member may have a plurality of receiving features. In the locked configuration, the locking posts may extend fully through the locking holes such that the tips are received in the receiving features to restrict relative motion between the base member and the guide member. In the unlocked configuration, the locking posts may be retracted such that the tips are withdrawn from the receiving features to enable relative motion between the base member and the guide member.

With the locking member in the unlocked configuration, the guide member may be movable from a first position to a second position, relative to the base member. The locking member may be actuatable to the locked configuration with the guide member in the first position to lock the guide member in the first position. The locking member may also be actuatable to the locked configuration with the guide member in the second position to lock the guide member in the second position.

With the locking member in the unlocked configuration, the guide member may further be movable to a third position, relative to the base member. The locking member may further be actuatable to the locked configuration with the guide member in the third position to lock the guide member in the third position.

The locking member may further have a first locking post and a second locking post, each of which has a tip. The base member may have a first locking hole that receives the first locking post and a second locking hole that receives the second locking post. The guide member may have a plurality of receiving features with at least a first receiving feature and a second receiving feature. In the locked configuration, with the guide member in the first position, the tip of the first locking post may be received in the first receiving feature to restrict relative motion between the base member and the guide member, and the tip of the second locking post may be received in the second receiving feature to further restrict relative motion between the base member and the guide member. In the locked configuration, with the guide member in the second position, the tip of the first locking post may be received one of the plurality of receiving features that is not the first receiving feature to restrict relative motion between the base member and the guide member. In the locked configuration, with the guide member in the third position, the tip of the second locking post may be received in one of the plurality of receiving features that is not the second receiving feature to restrict relative motion between the base member and the guide member. In the unlocked configuration, the first locking post and the second locking post may each be retracted such that the tips are withdrawn from the plurality of receiving features to enable relative motion between the base member and the guide member.

Further, according to some embodiments, a method may be designed to resect a tibia to prepare the tibia for attachment of a tibial prosthesis through use of a tibial resection guide with an anchoring assembly, a base member, a positioning assembly, and a guide member. The method may include using the anchoring assembly to secure the tibial resection guide to the tibia, and using the positioning assembly to adjustably position the base member proximate a tibial plateau of the tibia. The method may further include, with the tibial resection guide secured to the tibia and the base member positioned proximate the tibial plateau, with the guide member in a first position relative to the base member, inserting a cutting blade through a slot of the guide member to make a first cut in the tibia. The method may further include, after making the first cut, moving the guide member along an arcuate path around the tibial plateau to a second position, relative to the base member, and with the guide member in the second position, inserting the cutting blade through the slot again to make a second cut in the tibia such that the second cut intersects the first cut.

The base member may have a base member attachment feature. The guide member may have a guide member attachment feature. The guide member attachment feature may have a shape complementary to that of the base member attachment feature. Moving the guide member along an arcuate path around the tibial plateau to a second position, relative to the base member, may include sliding the guide member attachment feature along the base member attachment feature.

One of the base member attachment feature and the guide member attachment feature include a dovetail-shaped protrusion extending along a first arcuate pathway. The other of the base member attachment feature and the guide member attachment feature may include a dovetail-shaped recess extending along a second arcuate pathway. Moving the guide member along an arcuate path around the tibial plateau to a second position, relative to the base member, may further include causing the dovetail-shaped protrusion to slide along the dovetail-shaped recess.

The guide member may have one or more apertures. The method may further include, after moving the guide member to the second position and prior to making the second cut in the tibia, inserting one or more bone pins through the apertures and into the tibia to retain the guide member relative to the tibia.

The tibial resection guide may further have a locking member movably coupled to at least one of the base member and the guide member. The method may further include, prior to moving the guide member to the second position, actuating the locking member from a locked configuration, in which the guide member is fixedly secured to the base member, to an unlocked configuration, in which the guide member is movable along the arcuate path, relative to the base member.

The method may further include, after moving the guide member to the second position and prior to making the second cut in the tibia, actuating the locking member back to the locked configuration. The method may further include, after making the second cut in the tibia, actuating the locking member to the unlocked configuration and, with the locking member in the unlocked configuration, moving the guide member along the arcuate path around the tibial plateau to a third position, relative to the base member. The method may further include, after moving the guide member to the third position, actuating the locking member back to the locked configuration and, with the guide member in the third position and the locking member in the locked configuration, inserting the cutting blade through the slot again to make a third cut in the tibia such that the third cut intersects with the first cut.

The locking member may have a first locking post and a second locking post, each of which has a tip. The base member may have a first locking hole that receives the first locking post and a second locking hole that receives the second locking post. The guide member may have a first receiving feature and a second receiving feature. With the guide member in the first position, actuating the guide member to the unlocked configuration may include withdrawing the tip of the first locking post from the first receiving feature and withdrawing the tip of the second locking post from the second receiving feature to enable relative motion between the guide member and the base member. With the guide member in the second position, actuating the guide member to the locked configuration may include inserting the tip of the first locking post into the second receiving feature to restrict relative motion between the base member and the guide member. With the guide member in the third position, actuating the guide member to the locked configuration may include inserting the tip of the second locking post into the first receiving feature to restrict relative motion between the base member and the guide member.

Yet further, according to some embodiments, a tibial resection guide may be configured to facilitate resection of a tibia to prepare the tibia for attachment of a tibial prosthesis. The tibial resection guide may include an anchoring assembly that secures the tibial resection guide to the tibia, a base member, a positioning assembly extending between the anchoring assembly and the base member to adjustably position the base member proximate a tibial plateau of the tibia, a guide member with a slot sized to receive a cutting blade configured to resect the tibial plateau, and a locking member movably coupled to at least one of the base member and the guide member. The locking member may be actuatable between a locked configuration and an unlocked configuration. With the locking member in the locked configuration, the guide member may be fixedly secured to the base member. With the locking member in the unlocked configuration, the guide member may be movably coupled to the base member such that the guide member is movable along an arcuate path, relative to the base member, around the tibial plateau.

One of the base member and the guide member may include a dovetail-shaped protrusion extending along a first arcuate pathway. The other of the base member and the guide member may include a dovetail-shaped recess extending along a second arcuate pathway. The dovetail-shaped recess may slidably receive the dovetail-shaped protrusion. With the locking member in the unlocked configuration, the guide member may be movable from a first position to a second position and a third position, relative to the base member. The locking member may have a first locking post and a second locking post, each of which has a tip. The base member may have a first locking hole that receives the first locking post and a second locking hole that receives the second locking post. The guide member may have a plurality of receiving features including at least a first receiving feature and a second receiving feature. In the locked configuration, with the guide member in the first position, the tip of the first locking post may be received in the first receiving feature to restrict relative motion between the base member and the guide member, and the tip of the second locking post may be received in the second receiving feature to further restrict relative motion between the base member and the guide member. In the locked configuration, with the guide member in the second position, the tip of the first locking post may be received in one of the plurality of receiving features that is not the first receiving feature to restrict relative motion between the base member and the guide member. In the locked configuration, with the guide member in the third position, the tip of the second locking post may be received in one of the plurality of receiving features that is not the second receiving feature to restrict relative motion between the base member and the guide member. In the unlocked configuration, the first locking post and the second locking post may each be retracted such that the tips are withdrawn from the plurality of receiving features to enable relative motion between the base member and the guide member.

These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

FIGS. 5A through 5F are left, posterior, right, anterior, cephalad, and caudal views, respectively, of the tibial prosthesis of the knee arthroplasty system of FIG. 1.

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, system, and method, as represented in FIGS. 1 through 19, is not intended to limit the scope of the claims, as claimed, but is merely representative exemplary of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1:
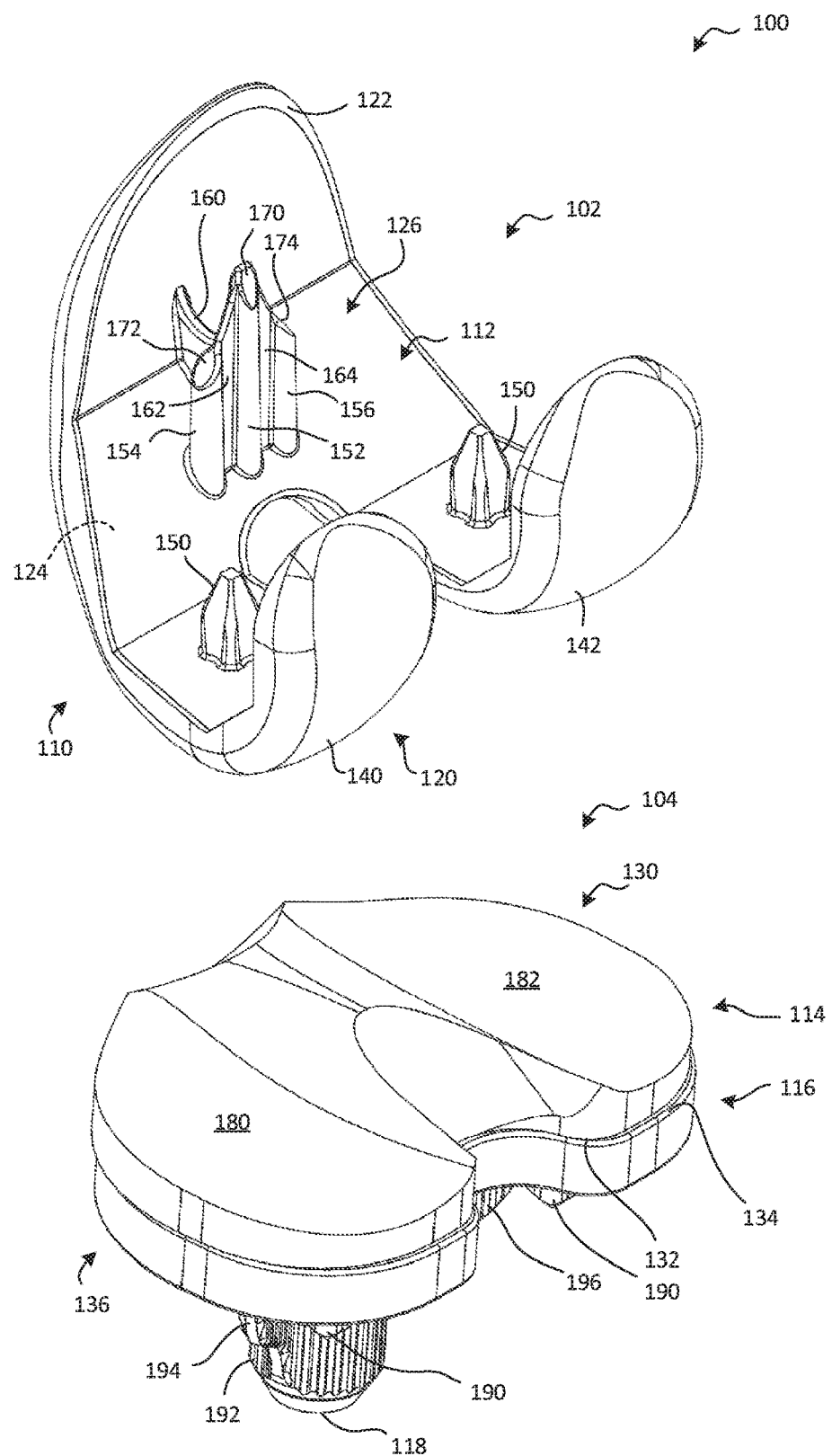
FIG. 1 is a perspective view of a knee arthroplasty system according to one embodiment.
Figure 2A:
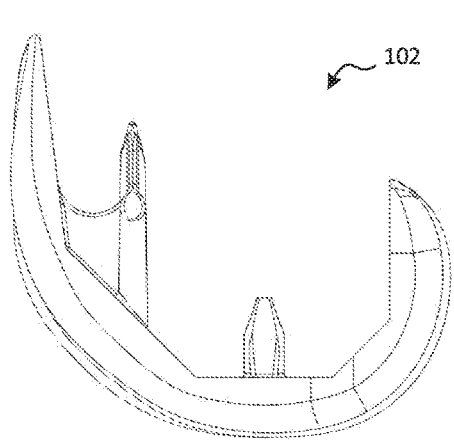
FIGS. 2A through 2F are left, posterior, right, anterior, cephalad, and caudal views, respectively, of the femoral prosthesis of the knee arthroplasty system of FIG. 1.
Figure 2B:
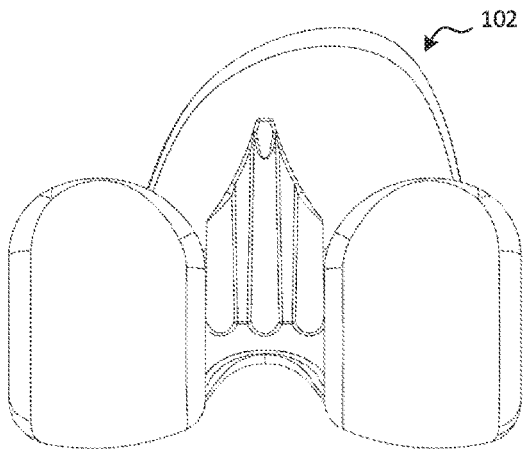
Figure 2C:
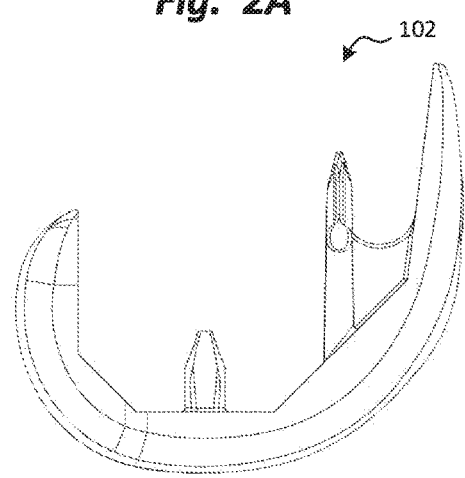
Figure 2D:
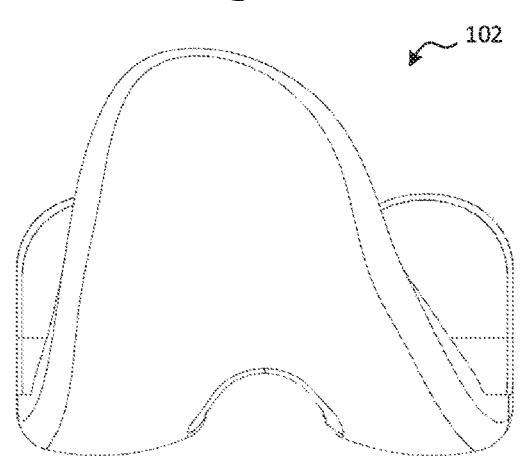
Figure 2E:
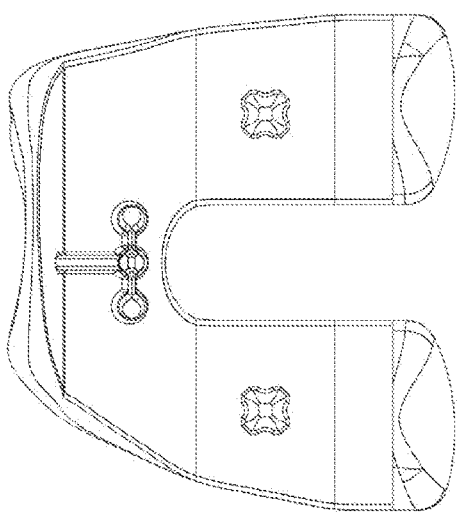
Figure 2F:
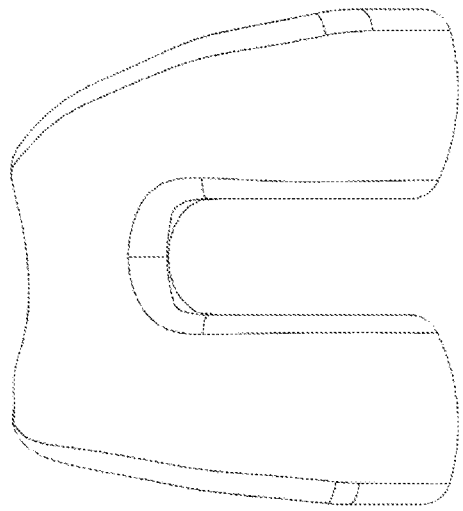

FIG. 1 is a perspective view of a knee arthroplasty system, or system 100, according to one embodiment. The system 100 may be designed to replace the natural articulating surfaces of a knee joint, and may thus have a femoral prosthesis 102 and a tibial prosthesis 104. In some embodiments, the system 100 may be designed to replace only the femoral or tibial articulating surfaces, and may thus include only the femoral prosthesis 102 or the tibial prosthesis 104.

The femoral prosthesis 102 and the tibial prosthesis 104 may each have an articulating component with replacement articulating surfaces, and a bone anchoring component secured to the articulating component to secure the articulating component to the underlying bone. Specifically, the femoral prosthesis 102 may have a femoral articulating component 110 and a femoral bone anchoring component 112. Similarly, the tibial prosthesis 104 may have a tibial articulating component 114 and a tibial bone anchoring component 116. The tibial prosthesis 104 may also have a tibial fastener 118.

Each of the aforementioned articulating components and bone anchoring components may have a joint-facing side and a bone-facing side. Thus, the femoral articulating component 110 may have a joint-facing side 120 and a bone-facing side 122, and the femoral bone anchoring component 112 may have a joint-facing side 124 and a bone-facing side 126. Similarly, the tibial articulating component 114 may have a joint-facing side 130 and a bone-facing side 132, and the tibial bone anchoring component 116 may have a joint-facing side 134 and a bone-facing side 136.

The bone-facing side 122 of the femoral articulating component 110 may have a shape that matches the shape of the joint-facing side 124 of the femoral bone anchoring component 112, and may be secured to the joint-facing side 124 of the femoral bone anchoring component 112 in a manner that will be set forth in greater detail subsequently. Similarly, the bone-facing side 132 of the tibial articulating component 114 may have a shape that matches the shape of the joint-facing side 134 of the tibial bone anchoring component 116, and may be secured to the joint-facing side 134 of the tibial bone anchoring component 116 in a manner that will be set forth in greater detail subsequently.

The joint-facing side 120 of the femoral articulating component 110 may have a first articulating surface 140 and a second articulating surface 142, which are shaped to mimic the shapes of the natural articulating surfaces on the end of the femur. The shapes depicted in FIG. 1 are merely exemplary; according to alternative embodiments, any articulating surface shape known in the art may be used.

The bone-facing side 126 of the femoral bone anchoring component 112 may have a plurality of features that enhance engagement of the femoral bone anchoring component 112 with the underlying bone. For example, the bone-facing side 126 of the femoral bone anchoring component 112 may have a pair of posts 150, a first femoral anchoring member 152, a second femoral anchoring member 154, and a third femoral anchoring member 156, which protrude from various surfaces of the bone-facing side 126 of the femoral bone anchoring component 112, as will be set forth in greater detail subsequently.

The first femoral anchoring member 152, the second femoral anchoring member 154, and the third femoral anchoring member 156 may be connected to each other and to the remainder of the bone-facing side 126 by a primary femoral web 160, a first femoral web 162, and a second femoral web 164. Specifically, the second femoral anchoring member 154 may be connected to the first femoral anchoring member 152 with the first femoral web 162, and the third femoral anchoring member 156 may be connected to the first femoral anchoring member 152 with the second femoral web 164. The first femoral anchoring member 152 may have a tip 170 with a tapered shape. The first femoral anchoring member 152, the first femoral web 162, and the second femoral anchoring member 154 may cooperate to define a first bevel 172. Similarly, the first femoral anchoring member 152, the second femoral web 164, and the third femoral anchoring member 156 may cooperate to define a second bevel 174.

The joint-facing side 130 of the tibial articulating component 114 may also have a first articulating surface 180 and a second articulating surface 182. After implantation of the femoral prosthesis 102 and the tibial prosthesis 104, the first articulating surface 140 may articulate with the first articulating surface 180, and the second articulating surface 142 may articulate with the second articulating surface 182. The articulation of the femoral articulating component 110 with the tibial articulating component 114 may be designed to mimic that of the natural knee joint.

The bone-facing side 136 of the tibial bone anchoring component 116 may have a plurality of posts 190 that protrude into the bone from the remainder of the bone-facing side 136. Further, the bone-facing side 136 of the tibial bone anchoring component 116 may have a central post 192 that also protrudes from the remainder of the bone-facing side 136. The central post 192 may further be connected to the remainder of the bone-facing side 136 by a first tibial web 194 and a second tibial web 196.

FIGS. 2A through 2F are left, posterior, right, anterior, cephalad, and caudal views, respectively, of the femoral prosthesis 102 of the system 100 of FIG. 1. These views further depict the various features described in connection with FIG. 1.

Figure 3:
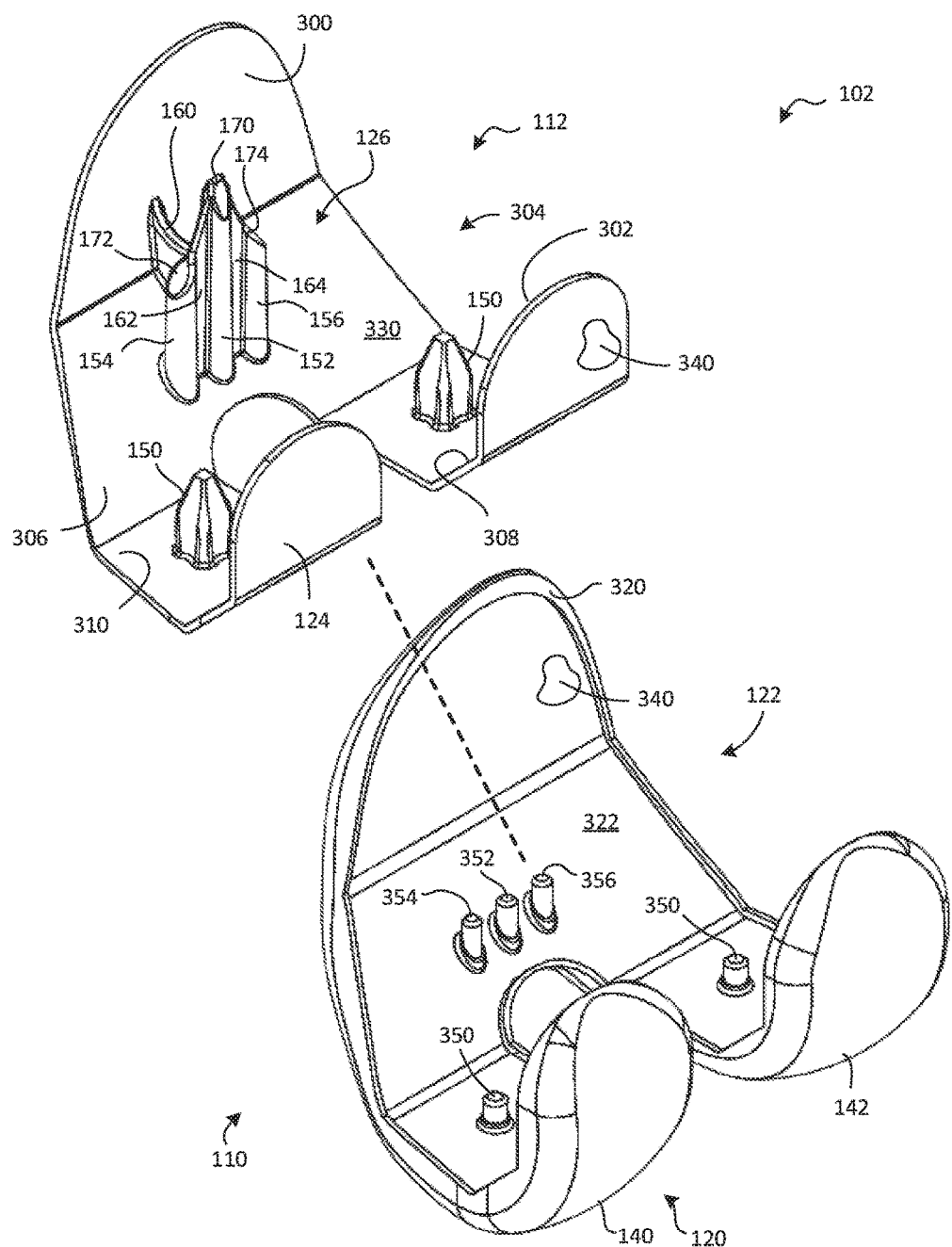
FIG. 3 is an exploded, perspective view of the femoral prosthesis of the knee arthroplasty system of FIG. 1.

FIG. 3 is an exploded, perspective view of the femoral prosthesis 102 of the system 100 of FIG. 1. The femoral articulating component 110 and the femoral bone anchoring component 112 may optionally be manufactured separately from each other. Accordingly, different manufacturing processes may be used to form the femoral articulating component 110 and the femoral bone anchoring component 112. This may advantageously enable the use of materials and/or processes for each of the femoral articulating component 110 and the femoral bone anchoring component 112 that are best suited for the role to be performed.

For example, the femoral articulating component 110 may be designed to endure cyclical loading in friction and compression. Accordingly, high-strength and/or low-wear materials and surface properties may be desired. Accordingly, the femoral articulating component 110 may be made of a relatively hard material such as an alloy of Cobalt Chromium ("Cobalt Chrome,"). Specifically, the femoral articulating component 110 may be made of an alloy of Cobalt Chromium Molybdenum (CoCrMo). A manufacturing process such as casting may be used. In some embodiments, the first articulating surface 140 and the second articulating surface 142 may be specially processed in a manner that increases their hardness and/or wear resistance.

Conversely, the femoral bone anchoring component 112 may be designed to provide high-strength fixation of the femoral articulating component 110 to the underlying bone. It may be desirable for the femoral bone anchoring component 112 to have a porous structure that encourages bone in-growth. Accordingly, the femoral bone anchoring component 112 may be formed of a metal such as Titanium, or specifically, direct metal laser sintered ("DMLS") Titanium. The femoral bone anchoring component 112 may be formed via an additive manufacturing method such as 3D printing. Such manufacturing methods may facilitate the creation of a porous structure, particularly on the bone-facing side 126 of the femoral bone anchoring component 112.

In some embodiments, the femoral bone anchoring component 112 may be made such that the porosity varies in a gradient through the thickness of the femoral bone anchoring component 112. Thus, the bone-facing side 126 of the femoral bone anchoring component 112 may be made more porous to facilitate bone in-growth, while the joint-facing side 124 of the femoral bone anchoring component 112 may be made less porous to enhance attachment of the joint-facing side 124 to the bone-facing side 122 of the femoral articulating component 110. In some embodiments, the joint-facing side 124 may be made substantially solid (i.e., nonporous) to enhance adhesion to the bone-facing side 122 of the femoral articulating component 110, while the bone-facing side 126 may be highly porous.

As shown, the bone-facing side 122 of the femoral articulating component 110 may have an anterior portion 300, a posterior portion 302, and a distal portion 304. Upon implantation of the femoral articulating component 110, the anterior portion 300 may be located on the anterior side of the knee, the posterior portion 302 may be located on the posterior side of the knee, and the distal portion 304 may be located at the distal end of the femur. The distal portion 304 may be divided into three faces: an anterior-distal face 306, a posterior-distal face 308, and a distal face 310. The anterior-distal face 306 may reside between the anterior portion 300 and the distal face 310, and the posterior-distal face 308 may be reside between the posterior portion 302 and the distal face 310.

As shown, the posts 150 may protrude from the distal face 310. The first femoral anchoring member 152, the second femoral anchoring member 154, and the third femoral anchoring member 156 may protrude from the posterior-distal face 308. The primary femoral web 160 may connect the first femoral anchoring member 152 to the anterior portion 300. The first femoral web 162 may connect the first femoral anchoring member 152 to the second femoral anchoring member 154 and to the anterior-distal face 306. Similarly, the second femoral web 164 may connect the first femoral anchoring member 152 to the third femoral anchoring member 156 and the anterior-distal face 306.

The first femoral anchoring member 152, the second femoral anchoring member 154, the third femoral anchoring member 156, the primary femoral web 160, the first femoral web 162, and the second femoral web 164 may cooperate to enhance engagement of the bone-facing side 126 of the femoral bone anchoring component 112 with the underlying bone. Specifically, these features may add to the surface area of the bone-facing side 126 in contact with the bone, providing a stronger bond with the bone via bone in-growth and/or application of bone cement. The position of these features on the anterior-distal face 306, proximate the anterior portion 300 may enable them to penetrate a relatively dense, sturdy bone mass proximate the distal end of the femur. Specifically, the bone that underlies the natural femoral articular surfaces to be replaced may, due to mechanical loading, have a denser structure and/or a thicker layer of cortical bone. Accordingly, the first femoral anchoring member 152, the second femoral anchoring member 154, the third femoral anchoring member 156, the primary femoral web 160, the first femoral web 162, and the second femoral web 164 may be optimally positioned for anchorage in strong, relatively dense bone that is likely to provide solid anchorage for the femoral bone anchoring component 112.

The posts 150, the first femoral anchoring member 152, the second femoral anchoring member 154, the third femoral anchoring member 156, the primary femoral web 160, the first femoral web 162, and the second femoral web 164 may all protrude in a cephalad direction so that these features can penetrate the bone, helping to anchor the femoral articulating component 110 on the distal end of the femur (not shown). These features may also be shaped to facilitate entry into and/or compaction of the bone.

Specifically, the tip 170, the first bevel 172, and the second bevel 174 may help to spread bone out of the path of the first femoral anchoring member 152, the second femoral anchoring member 154, the third femoral anchoring member 156, the first femoral web 162, and the second femoral web 164 as these features are pressed into the bone, thereby easing placement of the femoral prosthesis 102 on the distal end of the femur. Further, due to the presence of the tip 170, the first bevel 172, and/or the second bevel 174, the bone surrounding these features in their implanted state may be compacted and/or strengthened.

As also shown in FIG. 3, the bone-facing side 122 of the femoral articulating component 110 may have a peripheral ridge 320 that defines an interior recess 322. The shape of the interior recess 322 may closely match that of the joint-facing side 124 of the femoral bone anchoring component 112 so that the joint-facing side 124 of the femoral bone anchoring component 112 can be secured to the interior recess 322. When the femoral bone anchoring component 112 and the femoral articulating component 110 are assembled together, the bone-facing side 126 of the femoral bone anchoring component 112 may lie substantially flush with the peripheral ridge 320 of the bone-facing side 122 of the femoral articulating component 110.

In some embodiments, the bone-facing side 126 of the femoral bone anchoring component 112 may be treated to enhance porosity and/or bone in-growth. In some examples, the bone-facing side 126 of the femoral bone anchoring component 112 may be processed via a process such as anodizing to form Titanium Dioxide nanotubes on the bone-facing side 126. Specifically, the bone-facing side 126 may be anodized in a Fluoride electrolyte, as set forth in U.S. application Ser. No. 11/913,062, filed Jun. 10, 2008 and entitled "Compositions Comprising Nanostructures for Cell, Tissue and Artificial Organ Growth, and Methods for Making and Using Same, now U.S. Pat. No. 8,414,908, which is incorporated by reference as though set forth herein in its entirety. The result may be the formation of a surface layer 330 of Titanium Dioxide nanotubes on the bone-facing side 126.

The femoral articulating component 110 and the femoral bone anchoring component 112 may be secured together in a variety of ways. Such ways may include, but are not limited to, welding, brazing, press fitting, and the like. According to some embodiments, a substance 340 may be applied to one or both of the surfaces to be secured together via chemical and/or adhesive bonding. Any of the methods mentioned above may be used to secure the tibial articulating component 114 to the tibial bone anchoring component 116.

In addition to or in the alternative to the foregoing attachment methods, the methods disclosed in U.S. application Ser. No. 10/455,846, filed Jun. 6, 2003 and entitled "METHOD FOR ATTACHING A POROUS METAL LAYER TO A METAL SUBSTRATE," now U.S. Pat. No. 6,945,448, may be used. This application is incorporated as though set forth herein in its entirety.

Optionally, the surfaces to be bonded together may have features that facilitate and/or enhance the results of the bonding process. For example, the bone-facing side 122 of the femoral articulating component 110 may have features that cooperate with corresponding features (shown in FIG. 4) on the joint-facing side 124 of the femoral bone anchoring component 112 to help align the femoral articulating component 110 with the femoral bone anchoring component 112 and/or add mechanical fastening to the bonding described above. These features of the bone-facing side 122 may include a pair of post bosses 350, a first femoral anchoring member boss 352, a second femoral anchoring member boss 354, and a third femoral anchoring member boss 356.

Figure 4:
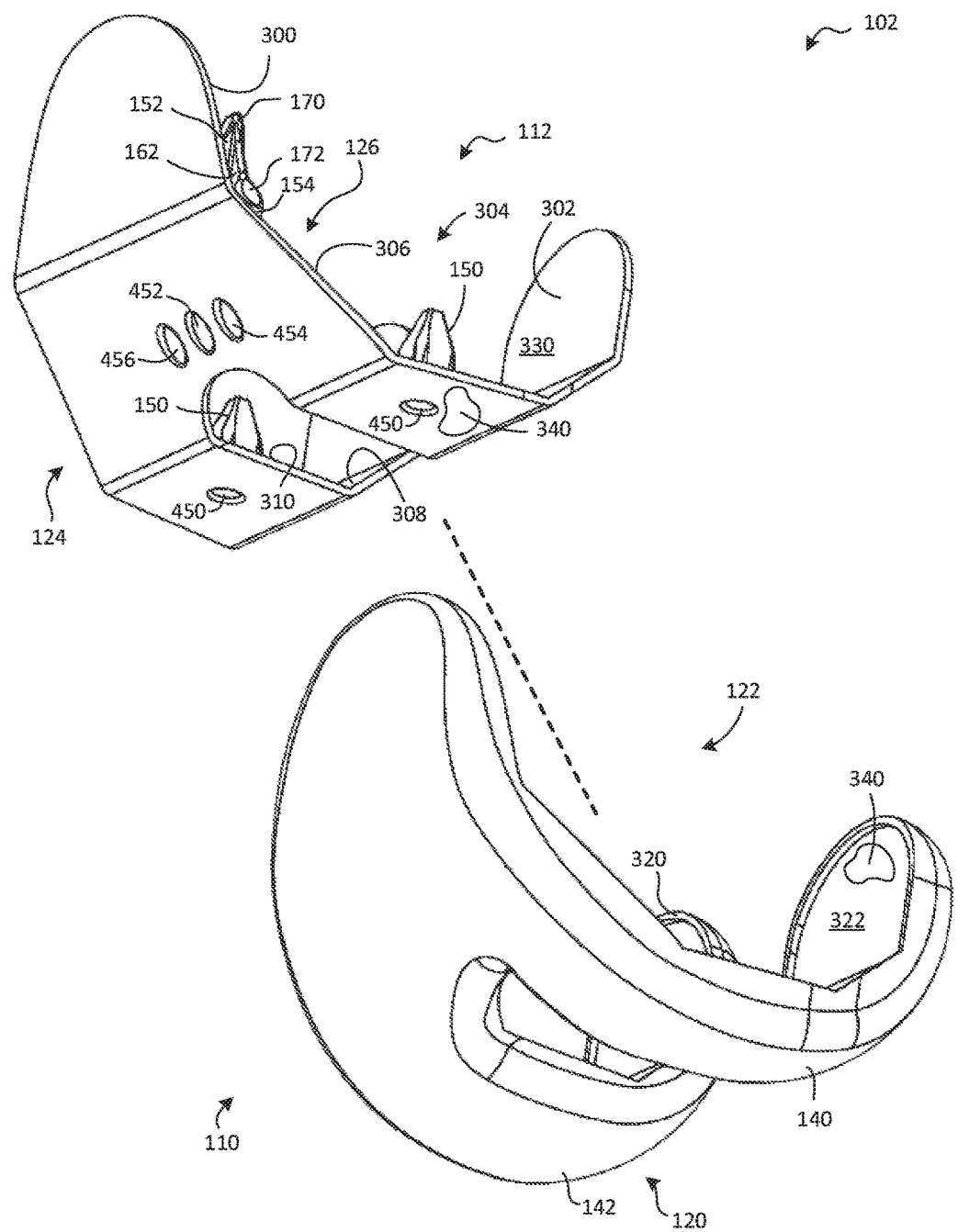
FIG. 4 is an exploded, perspective view, from a different viewpoint, of the femoral prosthesis of the knee arthroplasty system of FIG. 1.

FIG. 4 is an exploded, perspective view, from a different viewpoint, of the femoral prosthesis 102 of the system 100 of FIG. 1. The joint-facing side 124 of the femoral bone anchoring component 112 and the joint-facing side 120 of the femoral articulating component 110 are more clearly visible.

As shown, the joint-facing side 124 of the femoral bone anchoring component 112 may have features that cooperate with the post bosses 350, the first femoral anchoring member boss 352, the second femoral anchoring member boss 354, and the third femoral anchoring member boss 356 of the bone-facing side 122 of the femoral articulating component 110 depicted in FIG. 3. These features may include post bores 450, a first femoral anchoring member bore 452, a second femoral anchoring member bore 454, and a third femoral anchoring member bore 456. Each of the post bores 450 may reside in the interior of one of the posts 150. Similarly, the first femoral anchoring member bore 452, the second femoral anchoring member bore 454, and the third femoral anchoring member bore 456 may reside in the interiors of the first femoral anchoring member 152, the second femoral anchoring member 154, and the third femoral anchoring member 156, respectively.

The post bores 450 may be shaped to receive the post bosses 350. Similarly, the first femoral anchoring member bore 452, the second femoral anchoring member bore 454, and the third femoral anchoring member bore 456 may be shaped to receive the first femoral anchoring member boss 352, the second femoral anchoring member boss 354, and the third femoral anchoring member boss 356, respectively. If desired, the post bosses 350, the first femoral anchoring member boss 352, the second femoral anchoring member boss 354, and/or the third femoral anchoring member boss 356 may each be tapered to facilitate insertion into the post bores 450, the first femoral anchoring member bore 452, the second femoral anchoring member bore 454, and/or the third femoral anchoring member bore 456, respectively.

The features of the bone-facing side 122 may be received by these features of the joint-facing side 124 with some interference, which may cooperate with the bond described above to enhance attachment of the bone-facing side 122 to the joint-facing side 124. When the femoral articulating component 110 and the femoral bone anchoring component 112 are compressed together, as set forth above, the compression may be sufficient to urge the post bosses 350, the first femoral anchoring member boss 352, the second femoral anchoring member boss 354, and the third femoral anchoring member boss 356 into the post bores 450, the first femoral anchoring member bore 452, the second femoral anchoring member bore 454, and the third femoral anchoring member bore 456, respectively.

Additionally or alternatively, heat applied to the femoral articulating component 110 and/or the femoral bone anchoring component 112 may cause thermal expansion that eases insertion of the post bosses 350, the first femoral anchoring member boss 352, the second femoral anchoring member boss 354, and the third femoral anchoring member boss 356 into the post bores 450, the first femoral anchoring member bore 452, the second femoral anchoring member bore 454, and the third femoral anchoring member bore 456, respectively. The femoral articulating component 110 may be made such that the femoral articulating component 110 has higher thermal expansion than the femoral bone anchoring component 112. Thus, after insertion of the bosses into the bores, the femoral articulating component 110 and the femoral bone anchoring component 112 may be cooled, allowing the bores to tighten around the bosses.

In alternative embodiments, other positive and/or negative features may be used. Further, if desired, the positive features may be on the joint-facing side 124 of the femoral bone anchoring component 112, and the negative features may be on the bone-facing side 122 of the femoral articulating component 110.

FIGS. 5A through 5F are left, posterior, right, anterior, cephalad, and caudal views, respectively, of the tibial prosthesis 104 of the system 100 of FIG. 1. These views further depict the various features described in connection with FIG. 1.

Figure 6:
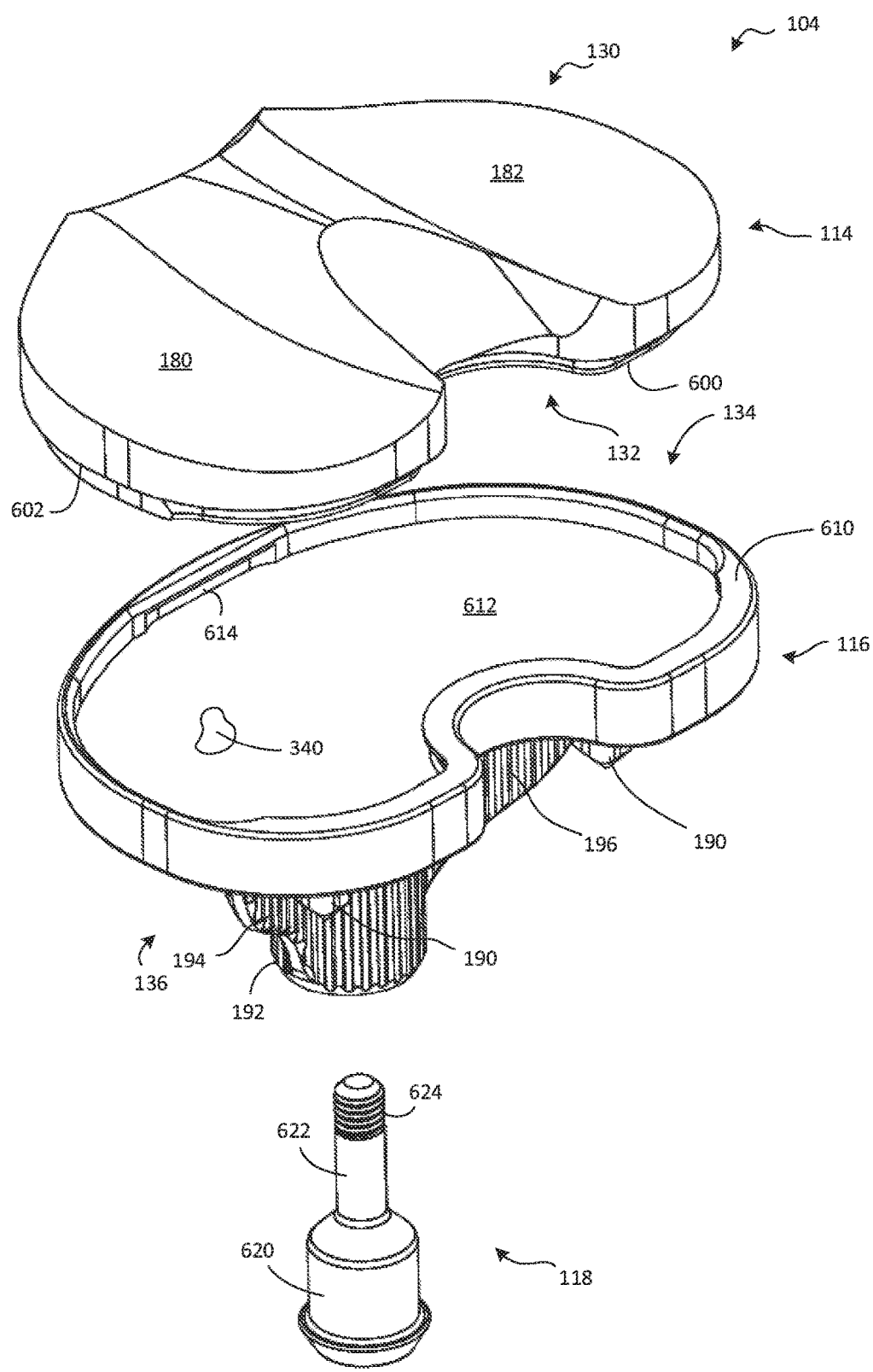
FIG. 6 is an exploded, perspective view of the tibial prosthesis of the knee arthroplasty system of FIG. 1.

FIG. 6 is an exploded, perspective view of the tibial prosthesis 104 of the system 100 of FIG. 1. As with the femoral prosthesis 102, the tibial articulating component 114 and the tibial bone anchoring component 116 may optionally be manufactured separately from each other. Accordingly, different manufacturing processes may be used to form the tibial articulating component 114 and the tibial bone anchoring component 116. For example, the tibial articulating component 114 may be formed via casting, and the tibial bone anchoring component 116 may be formed via additive manufacturing such as 3D printing.

Like the femoral articulating component 110, the tibial articulating component 114 may be made of Cobalt Chromium, or Cobalt Chromium Molybdenum. Similarly, like the femoral bone anchoring component 112, the tibial bone anchoring component 116 may be made of DMLS Titanium. A gradient of porosities may be present in the tibial bone anchoring component 116, with greater porosity on the bone-facing side 136, and lesser porosity on the joint-facing side 134. If desired, the joint-facing side 134 may be made substantially nonporous to enhance adhesion to the tibial articulating component 114, and the bone-facing side 136 may have a high level of porosity to promote bone in-growth.

As shown, the bone-facing side 132 of the tibial articulating component 114 may have a central plateau 600 that extends toward the tibial bone anchoring component 116, and a peripheral recess 602 that encircles the central plateau 600 and is recessed from the tibial bone anchoring component 116. The joint-facing side 134 of the tibial bone anchoring component 116 may have a shape that is complementary to that of the bone-facing side 132 of the tibial articulating component 114. Specifically, the joint-facing side 134 may have a peripheral ridge 610 that encircles an interior recess 612. An alcove 614 may extend into the peripheral ridge 610, from the space above the interior recess 612. When the tibial articulating component 114 and the tibial bone anchoring component 116 are assembled together, the central plateau 600 may be received within the interior recess 612, and the peripheral ridge 610 may engage the central plateau 600.

In some embodiments, the tibial articulating component 114 and the tibial bone anchoring component 116 may be secured together by the same bonding process described above in connection with the femoral articulating component 110 and the femoral bone anchoring component 112 of the femoral prosthesis 102, or with a modified version of such a bonding process. Thus, FIG. 6 depicts the exemplary application of the paste 340 to the interior recess 612 of the joint-facing side 134 of the tibial bone anchoring component 116.

FIG. 6 also depicts the tibial fastener 118 in greater detail. The tibial fastener 118 may have an enlarged head 620 and a shank 622 with threads 624 thereon that enable the tibial fastener 118 to threadably engage the tibial bone anchoring component 116, as will be discussed in greater detail subsequently.

Figure 7:
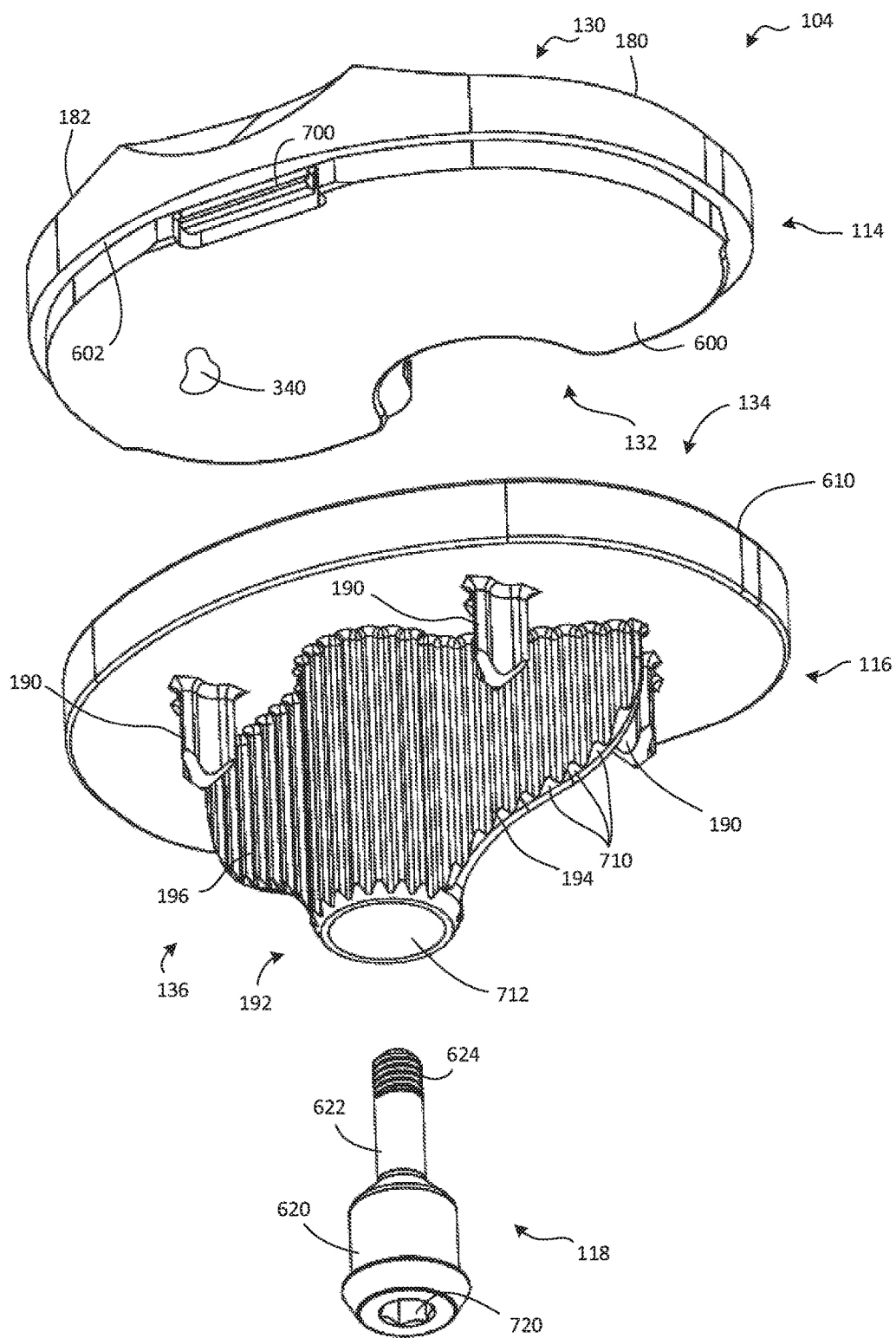
FIG. 7 is an exploded, perspective view, from a different viewpoint, of the tibial prosthesis of the knee arthroplasty system of FIG. 1.
Figure 8:
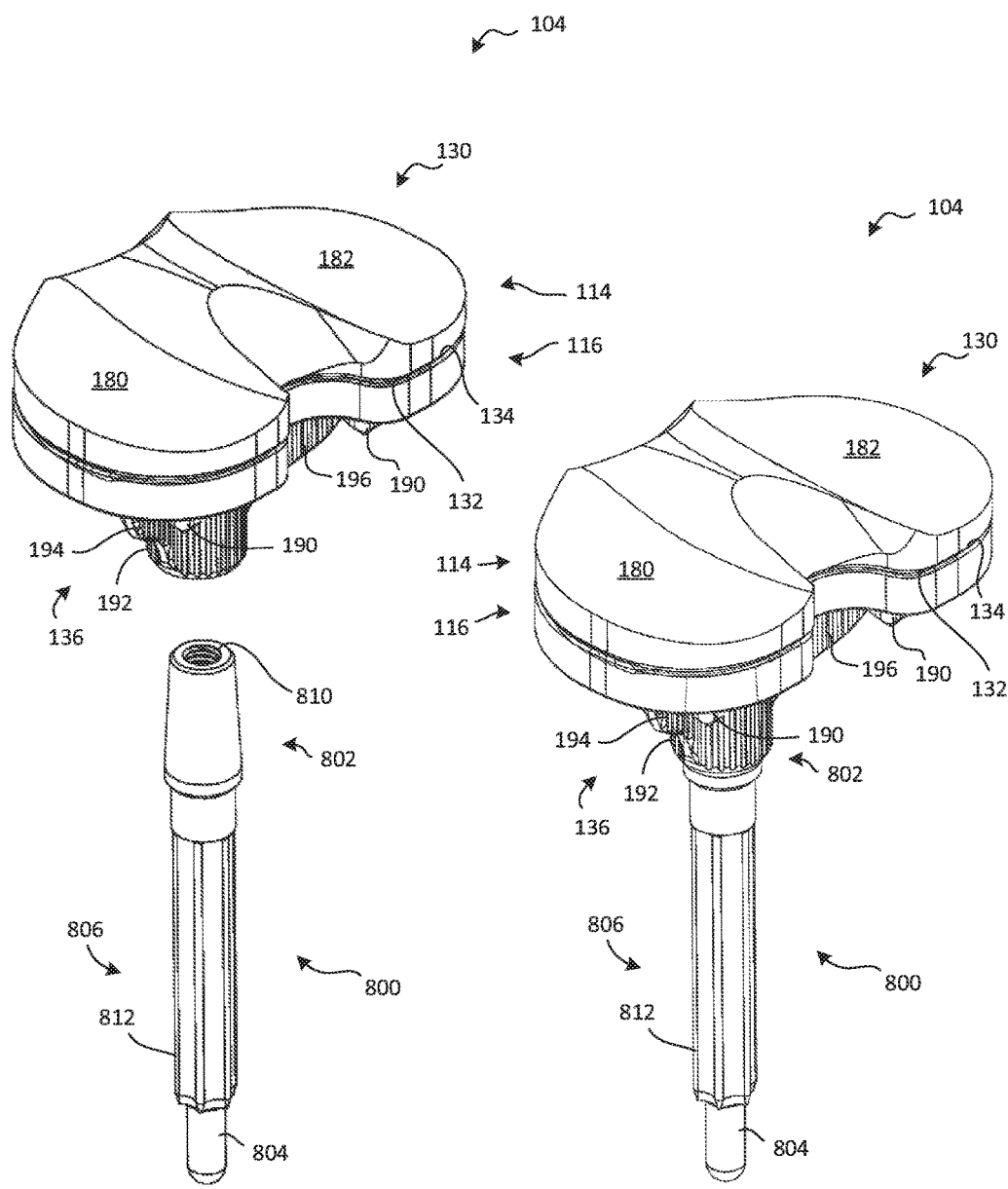
FIGS. 8A and 8B are exploded and fully-assembled perspective views, respectively, of the tibial prosthesis of FIG. 1, with an optional keel.

FIG. 7 is an exploded, perspective view, from a different viewpoint, of the tibial prosthesis 104 of the system 100 of FIG. 1. As shown, the central plateau 600 of the bone-facing side 132 of the tibial articulating component 114 may have a lip 700 that protrudes anteriorly. When the tibial articulating component 114 and the tibial bone anchoring component 116 are assembled, the lip 700 may protrude into the alcove 614 depicted in FIG. 6. Engagement of the lip 700 and the alcove 614 may further help to hold the anterior portions of the tibial articulating component 114 and the tibial bone anchoring component 116 together.

FIG. 7 also depicts the bone-facing side 136 of the tibial bone anchoring component 116 in greater detail. Four of the posts 190 may be present on the bone-facing side 136, and may help enhance the level of engagement of the bone-facing side 136 with the underlying bone, and in particular, with the cortical bone at the proximal end of the tibia. The central post 192, the first tibial web 194, and the second tibial web 196 may each extend distally from the remainder of the bone-facing side 136, and may cooperate to provide a greater surface area in engagement with the underlying bone. Thus, the central post 192, the first tibial web 194, and the second tibial web 196 may strengthen securement of the tibial anchoring component 116 to the tibia.

As shown, the central post 192, the first tibial web 194, and the second tibial web 196 may each have a crenellated shape, with crenellations 710 shown in FIG. 7. The crenellations 710 may further increase the surface area of the bone-facing side 136 in contact with the bone of the tibia, thereby further enhancing the potential for bone cement bonding and/or bone in-growth between the tibia and the bone-facing side 136. Further, if desired, the tibial bone anchoring component 116 may be processed as described above in the description of the femoral bone anchoring component 112, such that the tibial bone anchoring component 116 has a surface layer 330 formed of Titanium Dioxide nanotubes. Such a surface layer 330 may further enhance bone in-growth to further secure the bone-facing side 136 to the bone of the tibia.

As mentioned previously, the tibial articulating component 114 and the tibial bone anchoring component 116 may be secured together through the use of any of a variety of methods. Some of these are mentioned above in the description of assembly of the femoral articulating component 110 and the femoral bone anchoring component 112. Again, a substance 340 may optionally be applied to the bone-facing side 132 of the tibial articulating component 114 and/or to the joint-facing side 134 of the tibial bone anchoring component 116 to facilitate attachment via chemical and/or adhesive bonding.

As further shown in FIG. 7, the central post 192 may have a bore 712 that receives the tibial fastener 118. The bore 712 may have interior threads (not shown) that receive the threads 624 of the shank 622 of the tibial fastener 118. The tibial fastener 118 may serve to seal the bore 712 and reduce the chance of having toxins or microbes enter the bore 712 during implantation. The enlarged head 620 of the tibial fastener 118 may have a socket 720 with a hexagonal or other shape that can receive the shaped distal end of a removal tool (not shown), such as a hex key, to facilitate rotation of the tibial fastener 118 to remove the tibial fastener 118 from the bore 712.

FIGS. 8A and 8B are exploded and fully-assembled perspective views, respectively, of the tibial prosthesis 104 of FIG. 1, with an optional anchoring member in the form of a keel 800. The keel 800 may have a proximal end 802 and a distal end 804, with a shank 806 extending between the proximal end 802 and the distal end 804. The proximal end 802 may be shaped to be inserted into the bore 712 of the central post 192 of the tibial bone anchoring component 116 of the tibial prosthesis 104, as shown in FIG. 8B.

Specifically, the proximal end 802 may have a generally frustoconical shape. The walls of the bore 712 may define a similar, complementary shape. If desired, the proximal end 802 may be press-fitted into the bore 712. Additionally or alternatively, the proximal end 802 may have threads 810, which may engage corresponding threads (not shown) within the bore 712. In the alternative, the threads 810 may be used to receive another fastener (not shown), which may, in turn, be secured within the bore 712.

The tibial prosthesis 104 may be provided to the surgeon with the tibial fastener 118 in place within the bore 712. The surgeon may remove the tibial fastener 118 from the bore 712, and may insert and secure the proximal end 802 of the keel 800 within the bore 712. The intramedullary space of the tibia may be reamed and/or otherwise prepared to receive the keel 800 prior to attachment of the tibial prosthesis 104, with the keel 800, to the tibia.

The keel 800 may help provide additional bone engagement and/or rotational stability for the tibial prosthesis 104. Thus, the shank 806 may optionally have a plurality of splines 812 that protrude outward from the axis of the shank 806 to engage the surrounding bone. The splines 812 may increase the surface area of the keel 800 in contact with the bone to increase bone engagement, and may further resist rotation of the keel 800 within the bone. If desired, some or all of the keel 800 may have a porous structure that facilitates bone in-growth and/or bone cement engagement. Additionally or alternatively, the keel 800 may be anodized to form a surface layer 330, as set forth in connection with the femoral bone anchoring component 112 and the tibial bone anchoring component 116.

Figure 9:
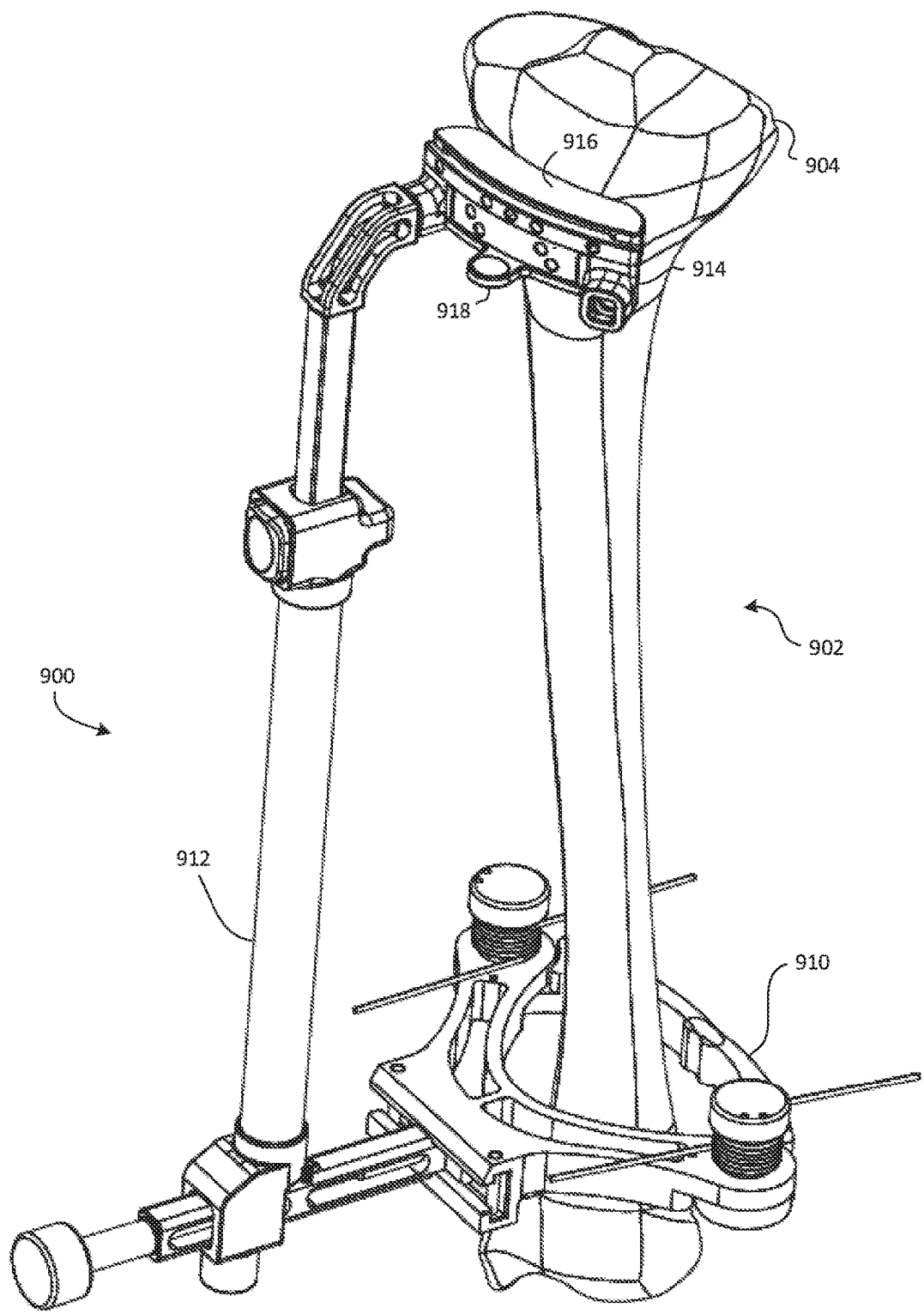
FIG. 9 is a perspective view of a tibial resection guide that may be used to prepare a tibia for implantation of the tibial prosthesis of the knee arthroplasty system of FIG. 1, according to one embodiment.

FIG. 9 is a perspective view of a tibial resection guide 900 that may be used to prepare a tibia 902 for implantation of the tibial prosthesis 104 of the system 100 of FIG. 1, according to one embodiment. The tibial resection guide 900 may be secured to the tibia 902 to facilitate resection of the tibial plateau 904 in preparation for attachment of the tibial prosthesis 104 in a position that will enable the tibial prosthesis 104 to effectively replace the natural articular surfaces of the tibial plateau 904.

As shown, the tibial resection guide 900 may have an anchoring assembly 910, a positioning assembly 912, a base member 914, a guide member 916, and a locking member 918. The anchoring assembly 910 may secure the tibial resection guide 900 to the tibia 902, for example, proximate the distal end, as shown. The positioning assembly 912 may have a plurality of links that are adjustably coupled to each other to facilitate adjustment of the position and/or orientation of the base member 914 relative to the anchoring assembly 910.

The guide member 916 may be slidably coupled to the base member 914, in a manner that will be set forth in greater detail below, to provide adjustable guidance for a cutting blade (shown in FIG. 18) that will be used to resect the tibial plateau 904. The locking member 918 may be used to selectively lock the guide member 916 in place relative to the base member 914, or allow the guide member 916 to slide relative to the base member 914.

Figure 10:
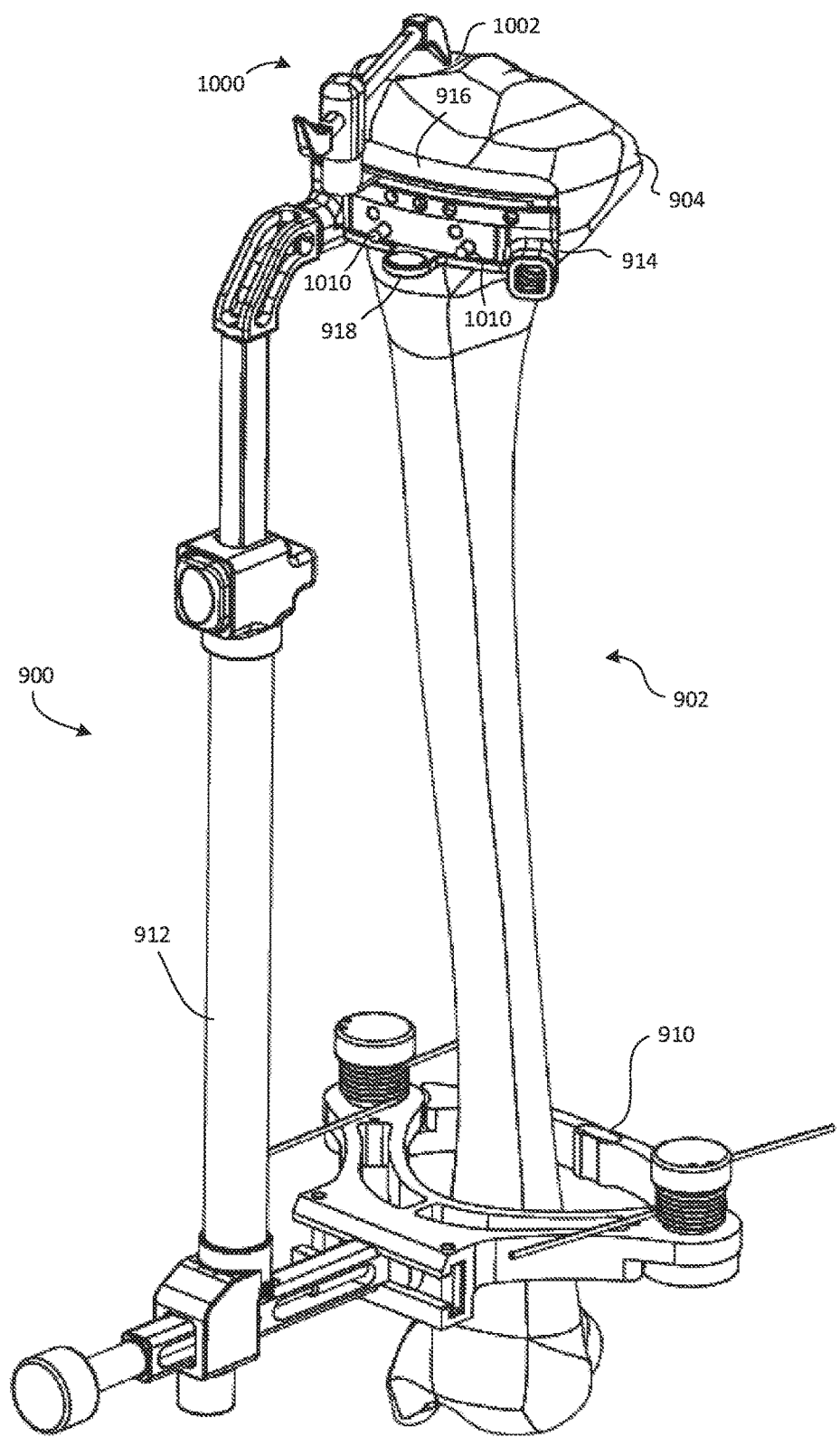
FIG. 10 is a perspective view of the tibial resection guide of FIG. 9, with an optional registration tool, according to one embodiment.

FIG. 10 is a perspective view of the tibial resection guide 900 of FIG. 9, with a registration member 1000, according to one embodiment. The registration member 1000 may be used to facilitate proper positioning of the base member 914, the guide member 916, and the locking member 918. The registration member 1000 may be coupled to the guide member 916 as shown, and may have a registration tip 1002 that can be located at a specific, predetermined location on the tibial plateau 904 while the position and/or orientation of the base member 914, the guide member 916, and the locking member 918 are adjusted.

After the proximal end of the tibia 902 has been exposed and the anchoring assembly 910 has been used to secure the tibial resection guide 900 to the tibia 902, the registration member 1000 may be coupled to the guide member 916, and the positioning assembly 912 may be moved to an unlocked configuration to permit the base member 914, the guide member 916, and the locking member 918 to be moved relative to the anchoring assembly 910. The various links of the positioning assembly 912 may be repositioned relative to each other as the registration member 1000, the base member 914, the guide member 916, and the locking member 918 are positioned and oriented.

Once the registration tip 1002 has reached the appropriate location on the tibial plateau 904, the positioning assembly 912 may be moved to a locked configuration to lock the position and/or orientation of the base member 914, the guide member 916, and the locking member 918 in place relative to the tibia 902. The registration member 1000 may then be removed. One or more bone pins 1010 may be inserted through the base member 914 to secure the base member 914 to the tibia 902.

Figure 11:
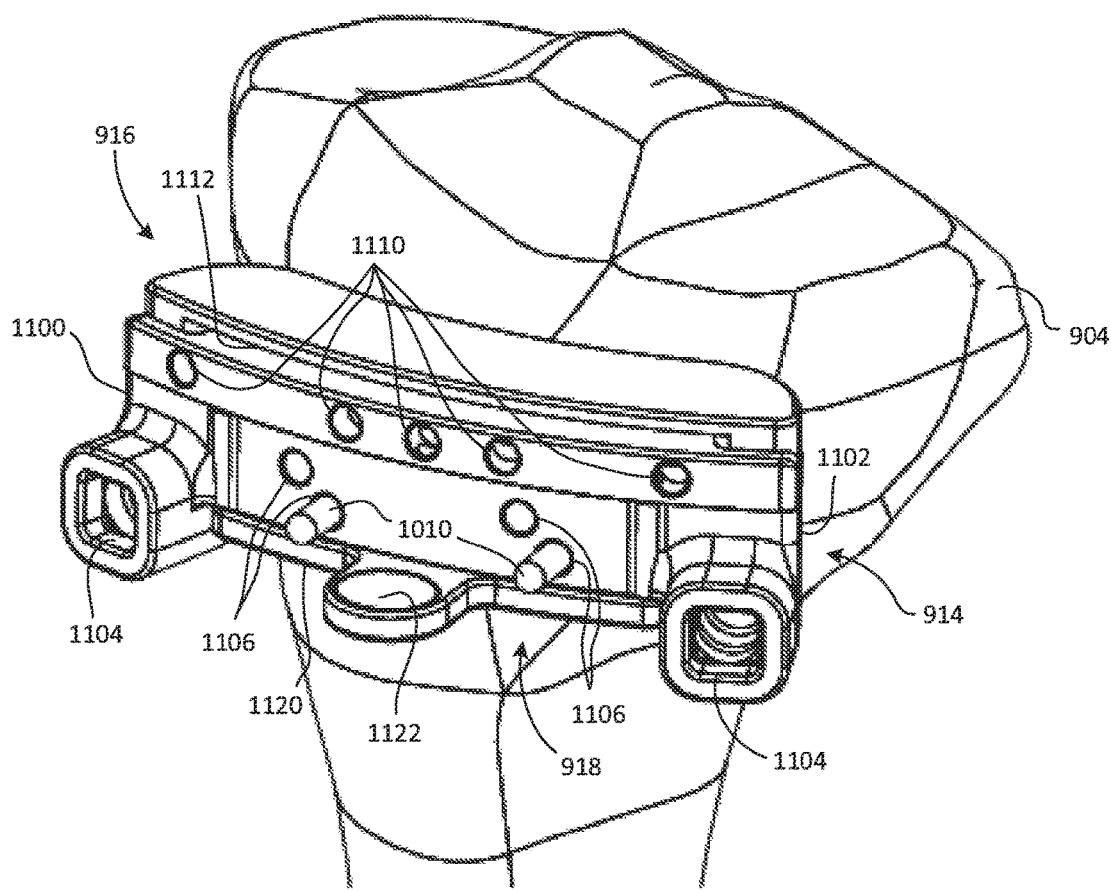
FIG. 11 is a perspective view of a portion of the tibial resection guide of FIG. 9, with the guide member in a first position relative to the base member, and the locking member in a locked configuration.

FIG. 11 is a perspective view of a portion of the tibial resection guide 900 of FIG. 9, with the guide member 916 in a first position relative to the base member 914, and the locking member 918 in a locked configuration. FIG. 11 depicts the base member 914, the guide member 916, and the locking member 918 in greater detail.

As shown, the base member 914 may have a first end 1100 and a second end 1102. The base member 914 may have two base member attachment features 1104, with one proximate the first end 1100 and the other proximate the second end 1102. The base member attachment features 1104 may be used to detachably secure the base member 914 to the positioning assembly 912. The presence of two of the base member attachment features 1104 may enable the base member 914 to be secured to the positioning assembly 912 in either of two relative positions. This may enable the tibial resection guide 900 to be easily adapted for use to guide resection of either of the left tibia or the right tibia.

The base member 914 may further have a plurality of apertures 1106 that extend through the depth of the base member 914, generally along radii extending outward from a central axis (not shown) of the tibia 902. Although any number of the apertures 1106 may be used, FIG. 11 depicts the presence of four of the apertures 1106, in two rows that are offset from each other. The bone pins 1010 may pass through two of the apertures 1106 in the same row to fix the position of the base member 914 relative to the tibial plateau 904.

The guide member 916 may also have a plurality of apertures 1110, which may extend through the depth of the guide member 916, generally along radii extending outward from the central axis of the tibia 902. Although any number of the apertures 1110 may be used, FIG. 11 depicts the presence of five of the apertures 1110, arranged in a single row. The apertures 1110 may initially be empty, as the position and orientation of the guide member 916 may be established by virtue of its attachment to the base member 914.

The guide member 916 may also have a slot 1112. The slot 1112 may pass through the depth of the guide member 916, and may have a width sufficient to guide a cutting blade used to resect the tibial plateau 904. Positioning the registration tip 1002 of the registration member 1000 in the manner shown in FIG. 10 may also position the slot 1112 in the proper location to guide the cutting blade to resect the tibial plateau 904 in the desired location.

The guide member 916 may be selectively movable relative to the base member 914, as will be shown and described subsequently. Thus, the guide member 916 may positionable in multiple different positions, relative to the base member 914, to facilitate proper resection of the tibial plateau 904. As depicted in FIG. 11, the guide member 916 may be in a first position, relative to the base member 914.

The locking member 918 may be used to selectively lock the guide member 916 in place relative to the base member 914. Specifically, the locking member 918 may have a locked configuration, in which the guide member 916 is fixedly secured to the base member 914, and an unlocked configuration, in which the guide member 916 is slidable relative to the base member 914. In FIG. 11, the locking member 918 is in the locked configuration. The locking member 918 may have a crossbar 1120 and a first tab 1122 extending from the crossbar 1120. The configuration and operation of the locking member 918 will be further shown and described in connection with FIG. 12.

Figure 12:
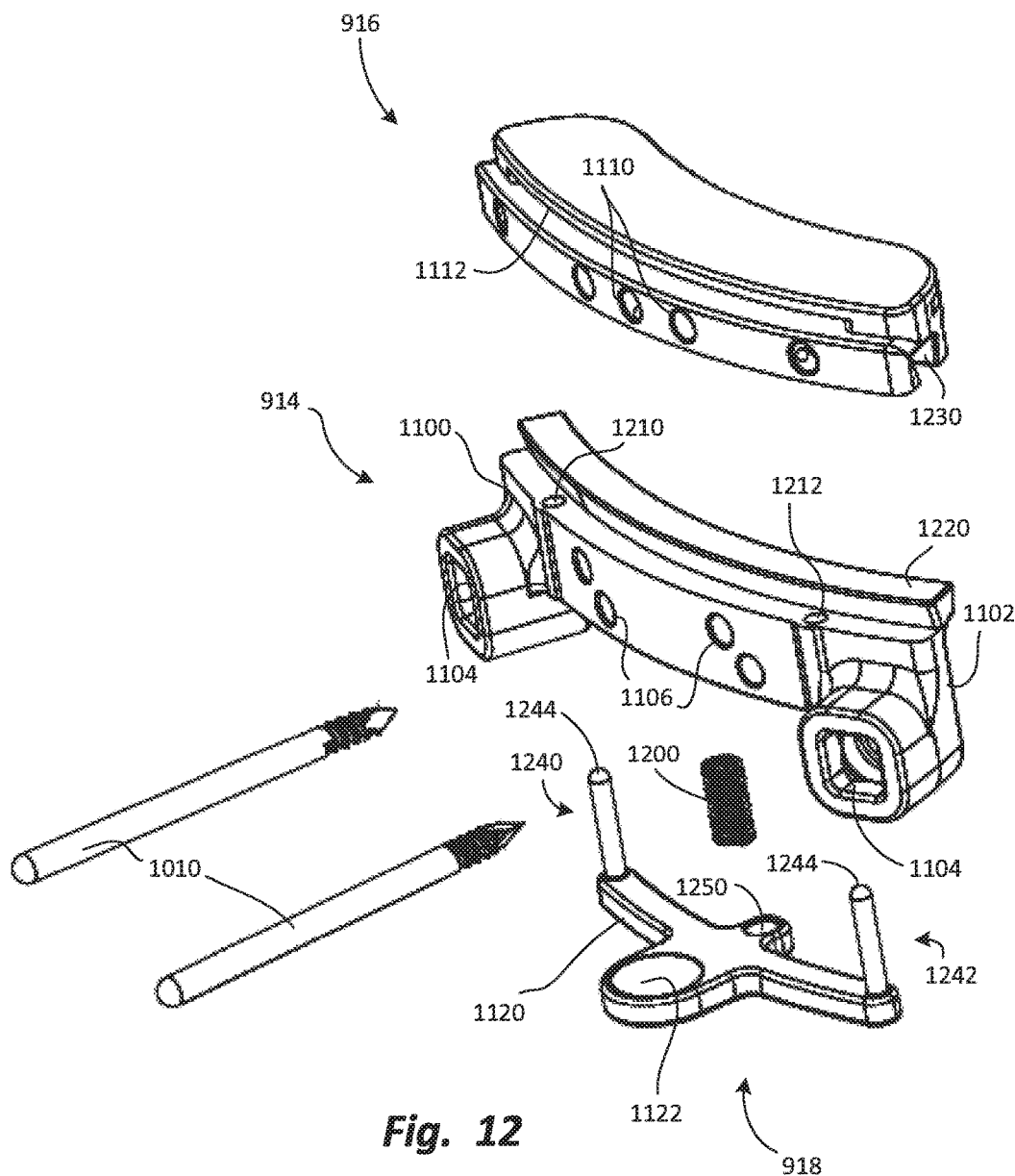
FIG. 12 is an exploded, perspective view of the portion of the tibial resection guide of FIG. 9, with two bone pins.

FIG. 12 is an exploded, perspective view of the portion of the tibial resection guide 900 of FIG. 9, with the two bone pins 1010 from FIGS. 10 and 11. The base member 914, the guide member 916, and the locking member 918 are all depicted in greater detail, along with a spring 1200 of the locking member 918.

As shown, the base member 914 may have a first locking hole 1210 and a second locking hole 1212. The first locking hole 1210 and the second locking hole 1212 may each extend through the entire height of the base member 914. The first locking hole 1210 and the second locking hole 1212 may enable the locking member 918 to selectively lock the position of the guide member 916 relative to the base member 914, as will be described subsequently.

Further, the base member 914 may have base member attachment feature shaped to engage a corresponding guide member attachment feature of the guide member 916. In the embodiment shown, the base member attachment feature may be a dovetail-shaped protrusion 1220, and the guide member attachment feature may be a dovetail-shaped recess 1230. The dovetail-shaped protrusion 1220 may be shaped to fit within the dovetail-shaped recess 1230. The dovetail shape of the dovetail-shaped protrusion 1220 and the dovetail-shaped recess 1230 may constrain relative motion between the base member 914 and the guide member 916 to sliding motion, i.e., motion by which the guide member 916 moves toward the first end 1100 or the second end 1102 of the base member 914.

The base member 914 and the guide member 916 may each have a generally arcuate shape. The dovetail-shaped protrusion 1220 and the dovetail-shaped recess 1230 may each extend along a corresponding arcuate pathway. Thus, the guide member 916 may slide along a corresponding arcuate pathway relative to the base member 914. This arcuate pathway may optionally be centered at or near the axis of the tibia 902.

In addition to the crossbar 1120 and the first tab 1122, the locking member 918 may have a first locking post 1240 and a second locking post 1242. The first locking post 1240 and the second locking post 1242 may each have a tip 1244. The first locking post 1240 and the second locking post 1242 may extend from the crossbar 1120 such that the first locking post 1240 extends into the first locking hole 1210 of the base member 914 and the second locking post 1242 extends into the second locking hole 1212 of the base member 914.

The locking member 918 may also have a second tab 1250 that extends in a direction opposite to that of the first tab 1122. The second tab 1250 may engage the spring 1200 in a manner that provides resilience to the operation of the locking member 918, as will be described subsequently.

Figure 13:
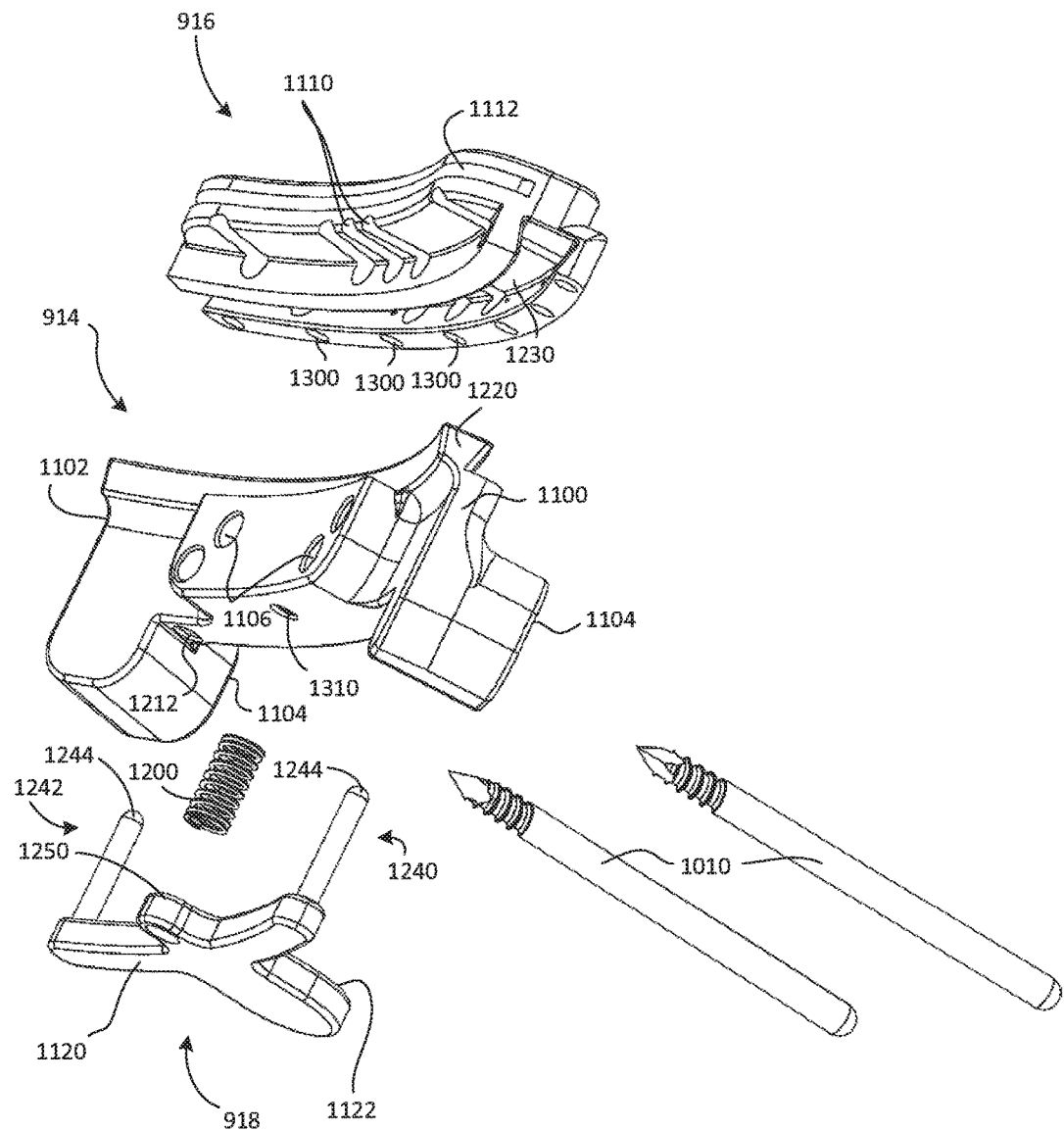
FIG. 13 is an exploded, perspective view, from an alternative viewpoint, of the portion of the tibial resection guide of FIG. 9, with the two bone pins.

FIG. 13 is an exploded, perspective view, from an alternative viewpoint, of the portion of the tibial resection guide 900 of FIG. 9, with the two bone pins 1010. As shown, the guide member 916 may have a plurality of receiving features 1300 arranged along its length. Each of the receiving features 1300 may be a blind hole shaped to receive the tip 1244 of either of the first locking post 1240 and the second locking post 1242. The receiving features 1300 may be spaced relatively evenly along the length of the guide member 916. In the embodiment of FIG. 9, there are seven of the receiving features 1300. However, in other embodiments, there may be different numbers of receiving features 1300, and they may be arranged in different patterns.

In the locked configuration, the crossbar 1120 may lie substantially flush with the adjoining surface of the base member 914. The first locking post 1240 and the second locking post 1242 may extend through the first locking hole 1210 and the second locking hole 1212, respectively, of the base member 914 so that tip 1244 of at least one of the first locking post 1240 and the second locking post 1242 resides in one of the receiving features 1300. Thus, the tip 1244 of one or both the first locking post 1240 and the second locking post 1242 may interfere, in the locked configuration, with sliding motion of the guide member 916 relative to the base member 914.

In the unlocked configuration, the crossbar 1120 may be displaced from the adjoining surface of the base member 914. The first locking post 1240 and the second locking post 1242 may be retracted such that the tip 1244 of the first locking post 1240 resides at least partially within the first locking hole 1210, and the tip 1244 of the second locking post 1242 resides at least partially within the second locking hole 1212. Thus, the tip 1244 of each of the first locking post 1240 and the second locking post 1242 may be retracted from engagement with the receiving features 1300, allowing the guide member 916 to slide relative to the base member 914.

The spring 1200 may serve to bias the locking member 918 toward the locked configuration. Specifically, the base member 914 may have a spring retention hole 1310 oriented toward the crossbar 1120 and the second tab 1250. The spring 1200 may have a first end that resides in the spring retention hole 1310, and a second end secured to the second tab 1250. The spring 1200 may be under tension such that the spring 1200 draws the second tab 1250 toward the base member 914. Thus, the spring 1200 may operate to urge the crossbar 1120, and thence the first locking post 1240 and the second locking post 1242, toward the base member 914, urging the locking member 918 toward the locked configuration.

Returning briefly to FIG. 11, the guide member 916 may be a first position relative to the base member 914, and the locking member 918 may be in the locked configuration. In the first position, the slot 1112 may be positioned to guide a cutting blade to resect a portion of the tibial plateau 904. The cutting blade may be used to make a first cut in the tibial plateau 904. However, the slot 1112 may not be sufficiently long to guide the cutting blade through the entire width of the tibial plateau 904 without being repositioned. Accordingly, it may be desirable to move the guide member 916 to one or more positions in addition to the first position.

In order to accomplish this, the locking member 918 may first be moved to the unlocked configuration. This may be done by grasping the first tab 1122 of the locking member 918, for example, with a thumb or finger, and urging the first tab 1122 away from the base member 914, against the resilient force of the spring 1200. This may cause the first locking post 1240 and the second locking post 1242 to be partially retracted through the first locking hole 1210 and the second locking hole 1212, respectively, thereby causing the tip 1244 of the first locking post 1240 and the tip 1244 of the second locking post 1242 to withdraw from the receiving features 1300 of the guide member 916.

The guide member 916 may then be grasped and urged to slide along the aforementioned arcuate pathway, either toward the first end 1100 or the second end 1102 of the base member 914. The clinician may optionally continue exerting pressure on the first tab 1122 of the locking member 918 until the base member 914 reaches the desired position relative to the guide member 916. Then, he or she may release the first tab 1122 to allow the locking member 918 to move back to the locked configuration, locking the guide member 916 in a second position relative to the base member 914.

If clinician does not continue exerting pressure on the first tab 1122 of the locking member 918 during sliding of the guide member 916 relative to the base member 914, the tip 1244 of the first locking post 1240 and the tip 1244 of the second locking post 1242 may slide along the surface of the guide member 916 facing the base member 914, between the receiving features 1300, until the guide member 916 reaches a position in which the tip 1244 of the first locking post 1240 and/or the tip 1244 of the second locking post 1242 are aligned with one or two of the receiving features 1300. The locking member 918 may then move back to the locked configuration by virtue of the resilient force exerted by the spring 1200, preventing further siding of the guide member 916 relative to the base member 914, locking the guide member 916 in the second position relative to the base member 914.

If further repositioning of the guide member 916 is desired, the clinician may again exert pressure on the first tab 1122 to move the locking member 918 to the unlocked configuration, and then continue sliding the guide member 916 relative to the base member 914. Notably, the tip 1244 of the first locking post 1240 and the tip 1244 of the second locking post 1242 need not both be engaged in the receiving features 1300 in order to lock the base member 914 in place. Rather, if the tip 1244 of either of the first locking post 1240 or the second locking post 1242 resides within one of the receiving features 1300, this may be sufficient to prevent further motion of the guide member 916 relative to the base member 914.

Figure 14:
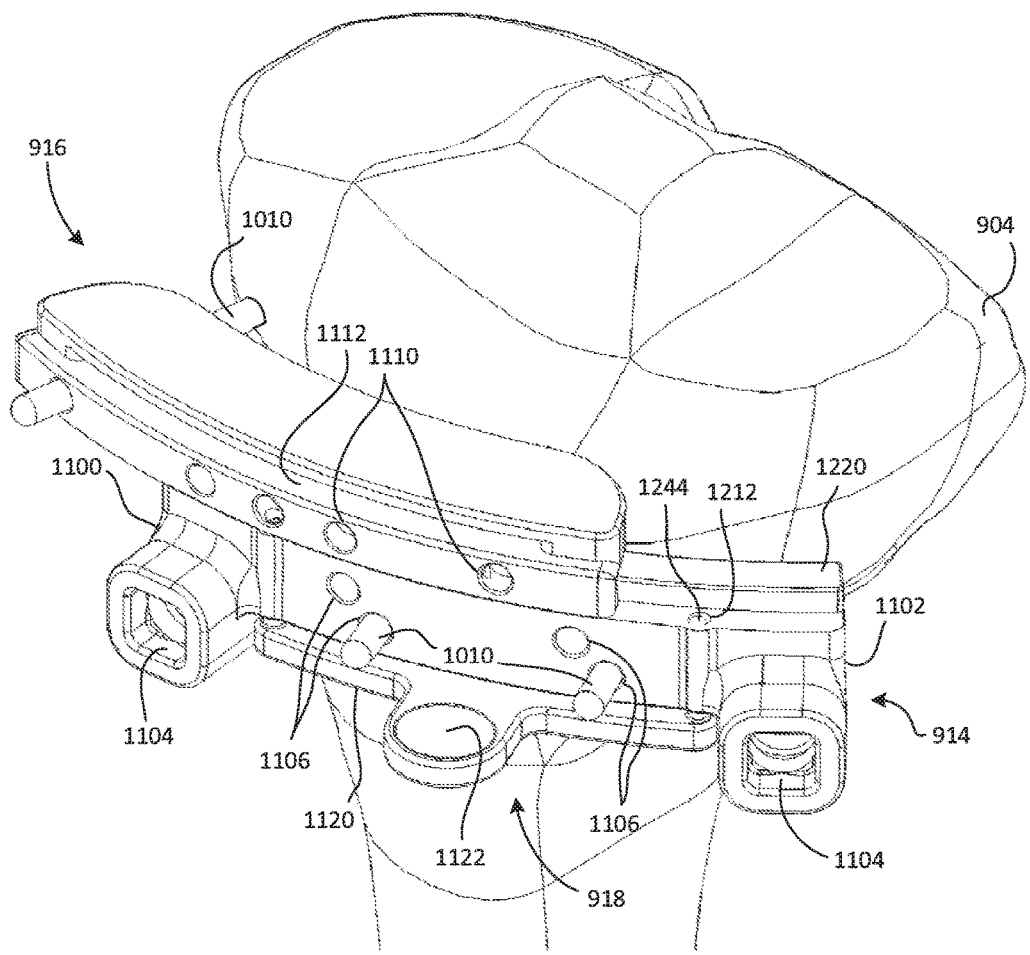
FIG. 14 is a perspective view of the portion of the tibial resection guide of FIG. 9, with the locking member in an unlocked configuration and the guide member in a second position relative to the base member.

FIG. 14 is a perspective view of the portion of the tibial resection guide 900 of FIG. 9, with the locking member 918 in an unlocked configuration and the guide member 916 in a second position relative to the base member 914. As mentioned previously, the crossbar 1120 may be displaced from the adjoining surface of the base member 914, and the tip 1244 of the first locking post 1240 and the tip 1244 of the second locking post 1242 may be retracted within the first locking hole 1210 and the second locking hole 1212, respectively, so such that they do not interfere with sliding motion of the guide member 916 relative to the base member 914.

Another of the bone pins 1010 may be used, either before or after the locking member 918 is returned to the locked configuration, to further secure the guide member 916 relative to the tibial plateau 904. It may be inserted through one of the apertures 1110 of the guide member 916 and into the tibial plateau 904.

Figure 15:
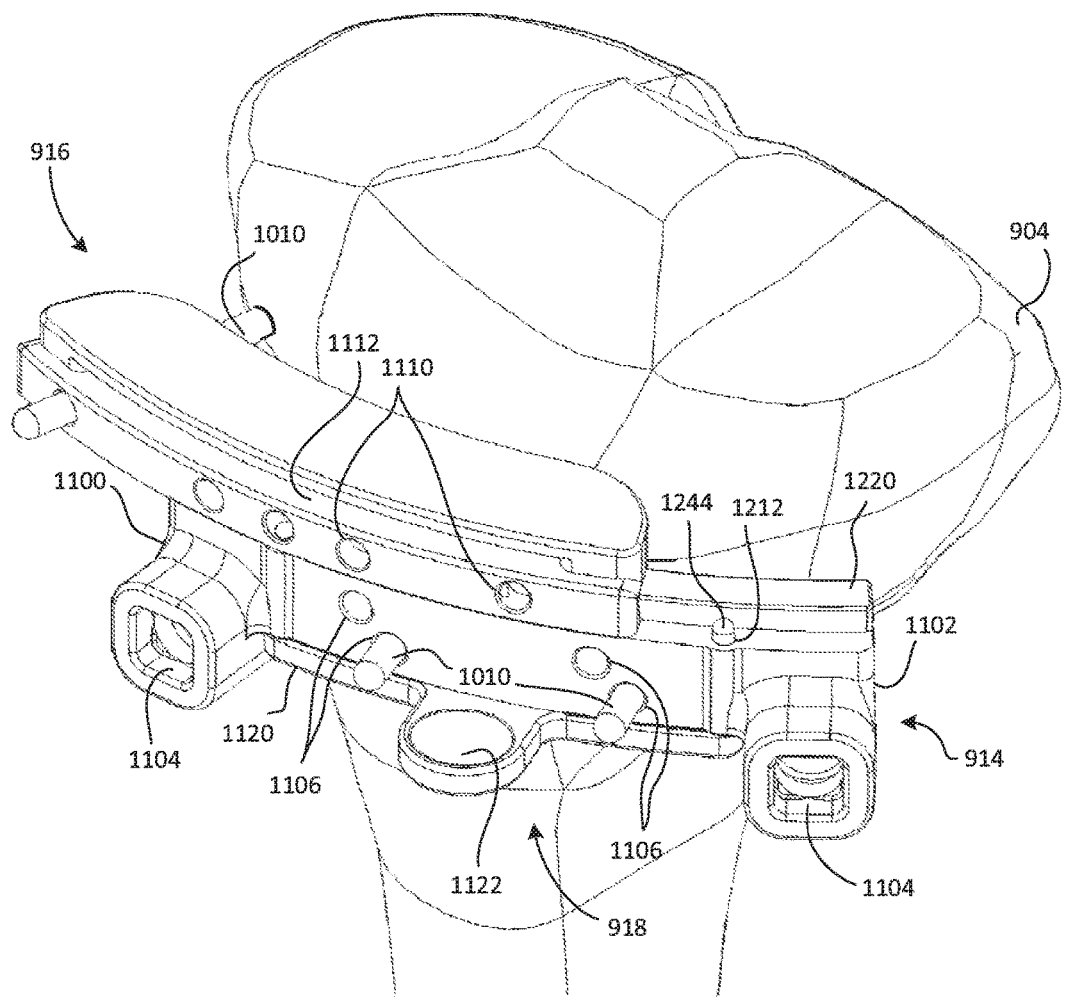
FIG. 15 is a perspective view of the portion of the tibial resection guide of FIG. 9, with the locking member in the locked configuration and the guide member in the second position relative to the base member.

FIG. 15 is a perspective view of the portion of the tibial resection guide 900 of FIG. 9, with the locking member 918 in the locked configuration and the guide member 916 in the second position relative to the base member 914. Further motion of the guide member 916 relative to the base member 914 may be restricted without moving the locking member 918 back to the unlocked configuration.

With the locking member 918 in the locked configuration and the additional fixation of the bone pins 1010 positioned in the apertures 1106 and the apertures 1110, the position of the guide member 916, relative to the tibial plateau 904, may be securely fixed. The cutting blade may again be inserted through the slot 1112 and used to make a second cut in the tibial plateau 904 with the guidance of the slot 1112. The second cut may intersect the first cut made previously. More specifically, the second cut may be substantially coplanar with the first cut.

In the event that the first and second cuts are sufficient to resect the tibial plateau 904, the tibial resection guide 900 may be removed, and no further cuts may be made. If the first and second cuts are not sufficient to resect the tibial plateau 904, the guide member 916 may again be repositioned relative to the base member 914. In order to accomplish this, the locking member 918 may again be moved to the unlocked configuration by exerting pressure on the first tab 1122 to urge the crossbar 1120 away from the base member 914 as discussed previously. The guide member 916 may then be moved such that it again slides along an arcuate pathway relative to the base member 914. The guide member 916 may be moved further in the same direction used to move the guide member 916 to the second position, or may be moved in the opposite direction, to reach a third position.

Figure 16:
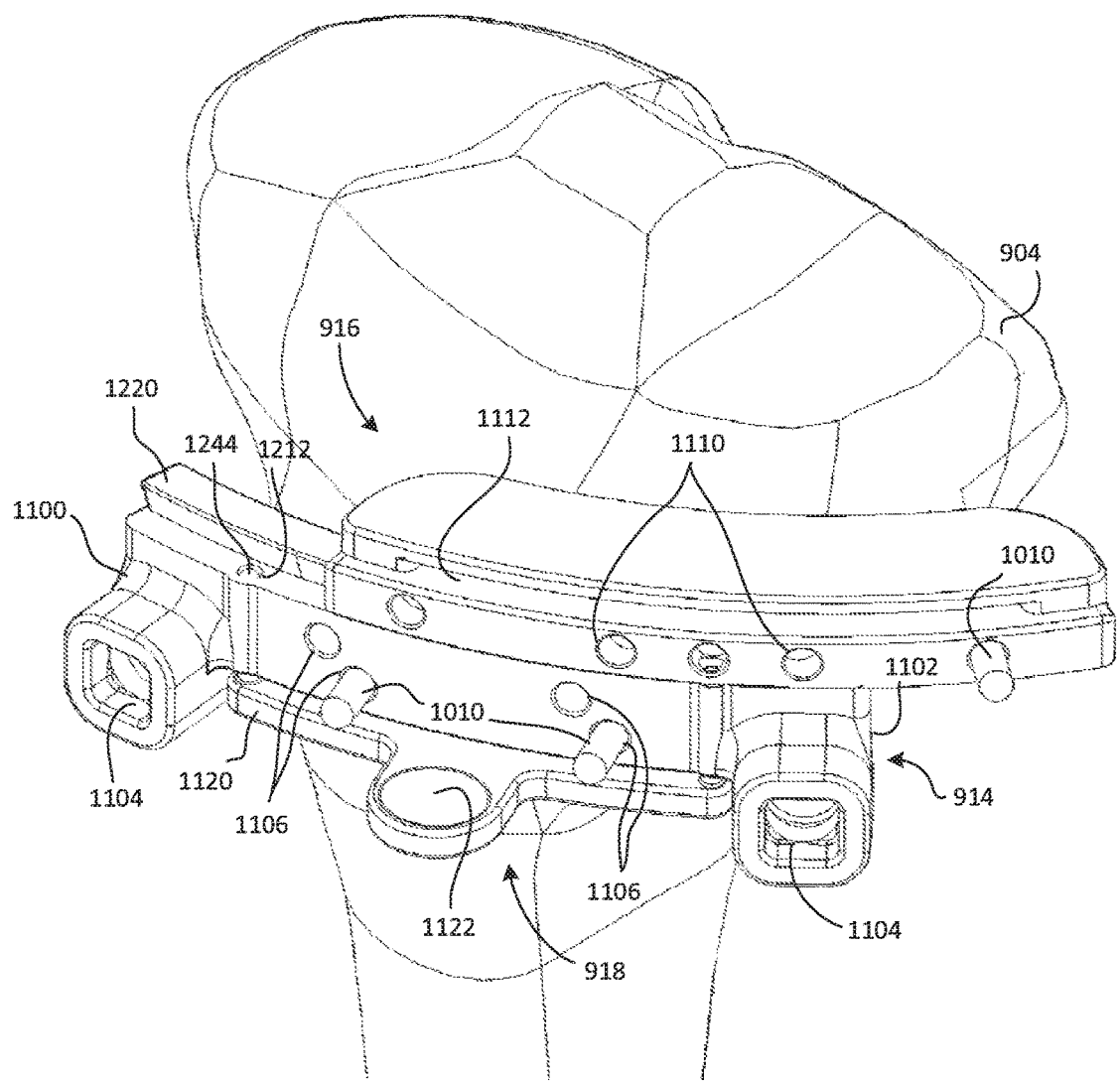
FIG. 16 is a perspective view of the portion of the tibial resection guide of FIG. 9, with the locking member in the unlocked configuration and the guide member in a third position relative to the base member.

FIG. 16 is a perspective view of the portion of the tibial resection guide 900 of FIG. 9, with the locking member 918 in the unlocked configuration and the guide member 916 in a third position relative to the base member 914. Again, another of the bone pins 1010 may be used, either before or after the locking member 918 is returned to the locked configuration, to further secure the guide member 916 relative to the tibial plateau 904. It may be inserted through one of the apertures 1110 of the guide member 916 and into the tibial plateau 904.

Figure 17:
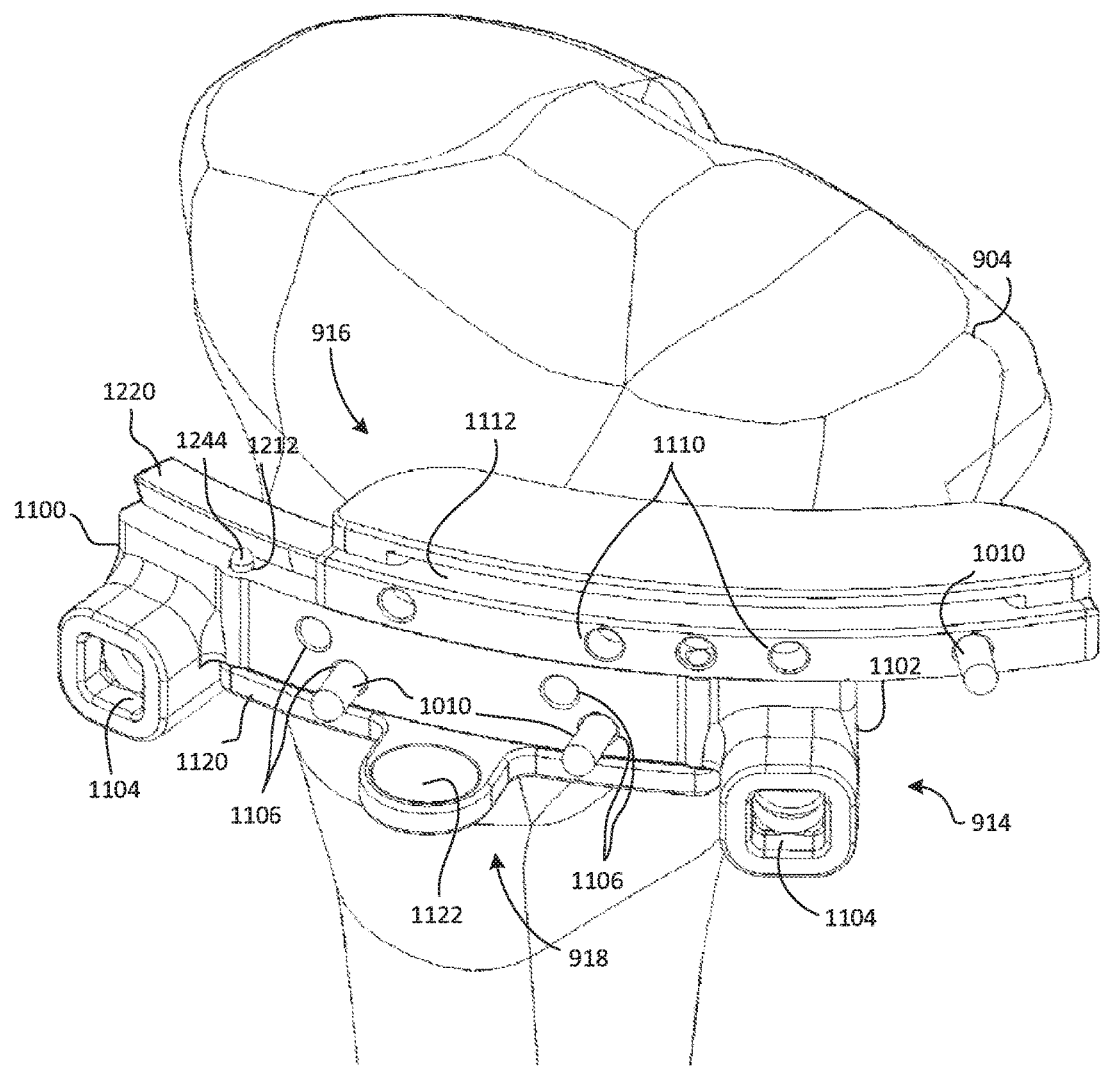
FIG. 17 is a perspective view of the portion of the tibial resection guide of FIG. 9, with the locking member in the locked configuration and the guide member in the third position relative to the base member.

FIG. 17 is a perspective view of the portion of the tibial resection guide 900 of FIG. 9, with the locking member 918 in the locked configuration and the guide member 916 in the third position relative to the base member 914. Further motion of the guide member 916 relative to the base member 914 may be restricted without moving the locking member 918 back to the unlocked configuration.

With the locking member 918 in the locked configuration and the additional fixation of the bone pins 1010 positioned in the apertures 1106 and the apertures 1110, the position of the guide member 916, relative to the tibial plateau 904, may again be securely fixed. The cutting blade may again be inserted through the slot 1112 and used to make a third cut in the tibial plateau 904 with the guidance of the slot 1112. Since, in the example of FIG. 17, the guide member 916 has been moved toward the first end 1100 of the base member 914 to reach the second position, and toward the second end 1102 of the base member 914 to reach the third position, the third cut may be made such that the third cut intersects the first cut. More specifically, the third cut may be substantially coplanar with the first and second cuts.

Figure 18:
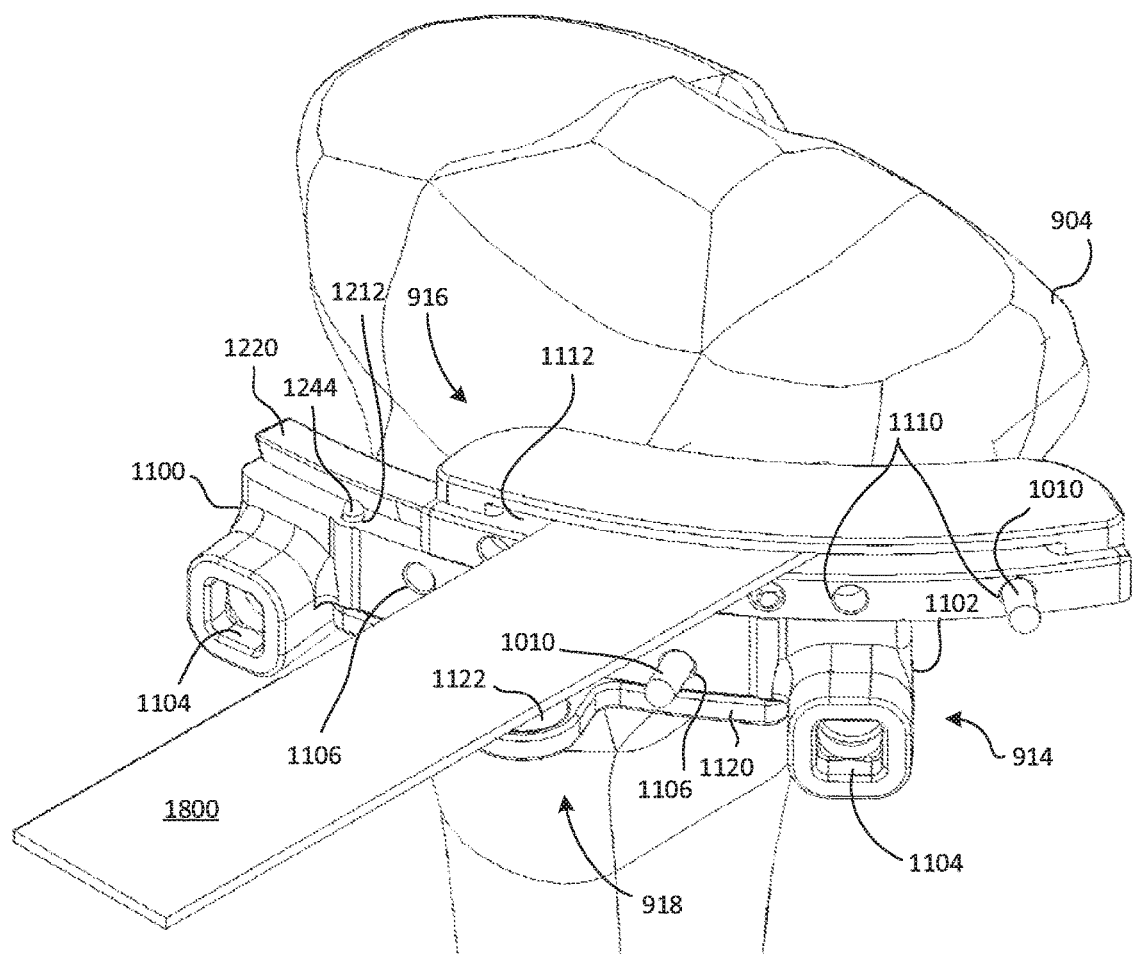
FIG. 18 is a perspective view of the portion of the tibial resection guide of FIG. 9, with the locking member in the locked configuration, with the guide member in the third position relative to the base member, and with a cutting blade passing through the slot of the guide member.

FIG. 18 is a perspective view of the portion of the tibial resection guide 900 of FIG. 9, with the locking member 918 in the locked configuration, with the guide member 916 in the third position relative to the base member 914, and with a cutting blade 1800 passing through the slot 1112 of the guide member 916 to make the third cut. The cutting blade 1800 may be part of a reciprocating bone saw or other tool, and may be manually driven or motor-driven.

In the event that the first, second, and third cuts are sufficient to resect the tibial plateau 904, the tibial resection guide 900 may be removed, and no further cuts may be made. If the first, second, and third cuts are not sufficient to resect the tibial plateau 904, the guide member 916 may again be repositioned relative to the base member 914 by unlocking the locking member 918 as set forth previously, and then sliding the guide member 916 relative to the base member 914 to a new, fourth position. A fourth cut may be made with the guide member 916 at the fourth position, and any number of additional cuts may be made as needed.

Figure 19:
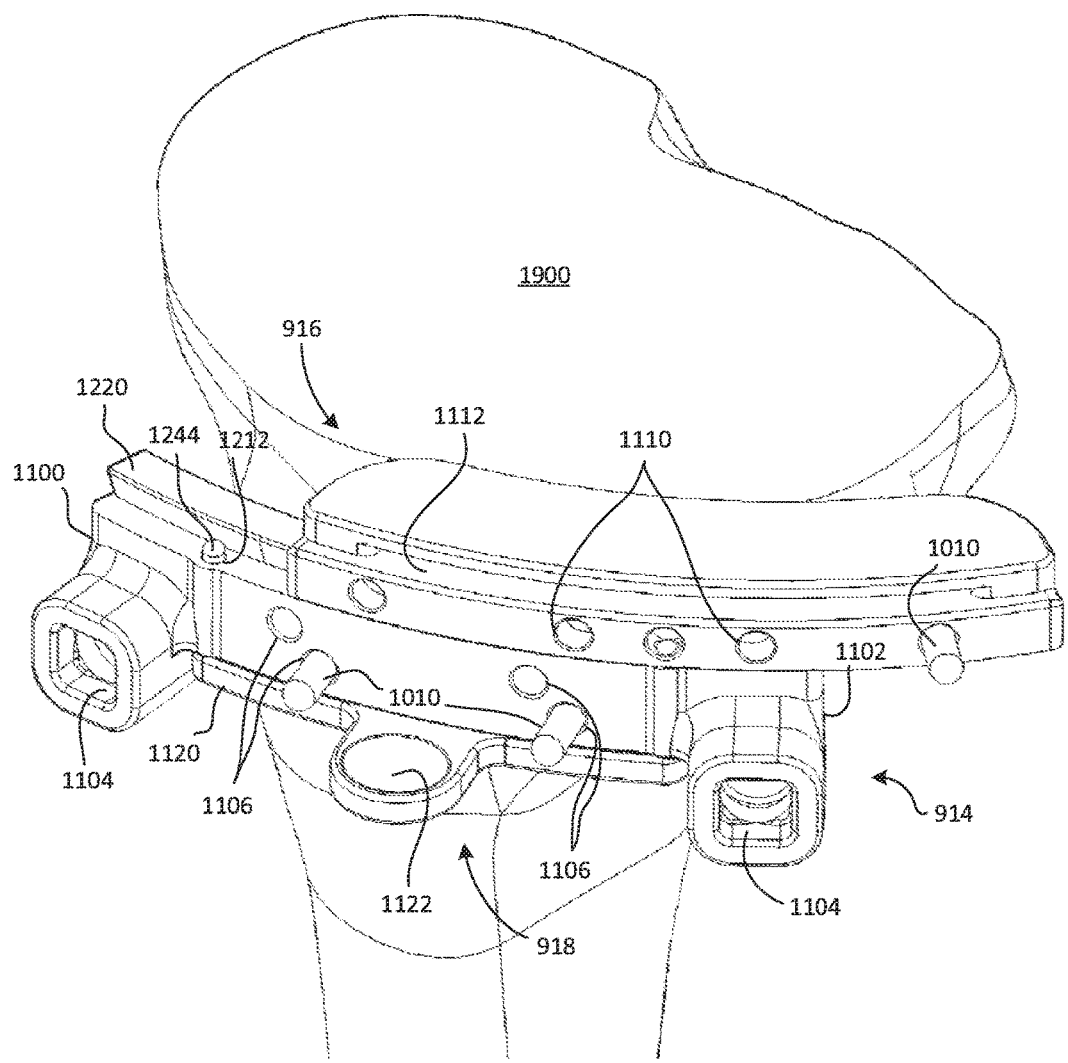
FIG. 19 is a perspective view of the portion of the tibial resection guide of FIG. 9, with the locking member in the locked configuration, with the guide member in the third position relative to the base member, and with the tibial plateau resected away in preparation for implantation of the tibial implant of FIG. 1.

FIG. 19 is a perspective view of the portion of the tibial resection guide 900 of FIG. 9, with the locking member 918 in the locked configuration, with the guide member 916 in the third position relative to the base member 914, and with the tibial plateau resected in preparation for implantation of the tibial implant of FIG. 1. The result may be the presence of a resection surface 1900 on the proximal end of the tibia 902. Once resection of the tibia 902 is complete, the tibial resection guide 900 may be removed from the tibia 902 by removing the bone pins 1010 and detaching the anchoring assembly 910 from the tibia 902.

The resection surface 1900 may be substantially planar, and may be further modified via reaming and/or other operations to prepare the resection surface 1900 to receive the bone-facing side 136 of the tibial bone anchoring component 116 of the tibial prosthesis 104. The tibial prosthesis 104 may then be secured to the tibia 902.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the methods and systems disclosed herein.

What is claimed is:

1. A tibial resection guide configured to facilitate resection of a tibia to prepare the tibia for attachment of a tibial prosthesis, the tibial resection guide comprising: an anchoring assembly that secures the tibial resection guide to the tibia; a base member; a positioning assembly extending between the anchoring assembly and the base member to adjustably position the base member proximate a tibial plateau of the tibia; and a guide member comprising a slot sized to receive a cutting blade configured to resect the tibial plateau; wherein the guide member is movably coupled to the base member such that the guide member is movable along an arcuate path, relative to the base member, around the tibial plateau, wherein: the base member comprises a base member attachment feature; the guide member comprises a guide member attachment feature; and the guide member attachment feature has a shape complementary to that of the base member attachment feature such that the guide member attachment feature and the base member attachment feature cooperate to slidably couple the guide member to the base member.

2. The tibial resection guide of claim 1, wherein:
one of the base member attachment feature and the guide member attachment feature comprises a dovetail-shaped protrusion extending along a first arcuate pathway;
the other of the base member attachment feature and the guide member attachment feature comprises a dovetail-shaped recess extending along a second arcuate pathway; and
the dovetail-shaped recess slidably receives the dovetail-shaped protrusion.

3. The tibial resection guide of claim 1, wherein the guide member comprises a plurality of apertures through which bone pins can be inserted into the tibia to retain the guide member relative to the tibia.

4. The tibial resection guide of claim 1, wherein the base member comprises two base member attachment features positioned proximate two opposing ends of the base member, wherein the positioning assembly is attachable to either of the base member attachment features.

5. The tibial resection guide of claim 1, further comprising a locking member movably coupled to at least one of the base member and the guide member;
wherein:
the locking member is actuatable between a locked configuration and an unlocked configuration;
with the locking member in the locked configuration, the guide member is fixedly secured to the base member; and
with the locking member in the unlocked configuration, the guide member is movable along the arcuate path, relative to the base member.

6. The tibial resection guide of claim 5, wherein:
with the locking member in the unlocked configuration, the guide member is movable from a first position to a second position, relative to the base member;
the locking member is actuatable to the locked configuration with the guide member in the first position to lock the guide member in the first position; and
the locking member is also actuatable to the locked configuration with the guide member in the second position to lock the guide member in the second position.

7. The tibial resection guide of claim 6, wherein:
with the locking member in the unlocked configuration, the guide member is further movable to a third position, relative to the base member; and
the locking member is further actuatable to the locked configuration with the guide member in the third position to lock the guide member in the third position.

8. The tibial resection guide of claim 7, wherein:
the locking member comprises a first locking post and a second locking post, each of which comprises a tip;
the base member comprises a first locking hole that receives the first locking post and a second locking hole that receives the second locking post;
the guide member comprises a plurality of receiving features comprising at least a first receiving feature and a second receiving feature;
in the locked configuration, with the guide member in the first position, the tip of the first locking post is received in the first receiving feature to restrict relative motion between the base member and the guide member, and the tip of the second locking post is received in the second receiving feature to further restrict relative motion between the base member and the guide member;
in the locked configuration, with the guide member in the second position, the tip of the first locking post is received one of the plurality of receiving features that is not the first receiving feature to restrict relative motion between the base member and the guide member;
in the locked configuration, with the guide member in the third position, the tip of the second locking post is received in one of the plurality of receiving features that is not the second receiving feature to restrict relative motion between the base member and the guide member; and
in the unlocked configuration, the first locking post and the second locking post are each retracted such that the tips are withdrawn from the plurality of receiving features to enable relative motion between the base member and the guide member.

9. The tibial resection guide of claim 5, wherein:
the locking member comprises a plurality of locking posts, each of which comprises a tip;
the base member comprises a plurality of locking holes, each of which receives one of the locking posts;
the guide member comprises a plurality of receiving features;
in the locked configuration, the locking posts extend fully through the locking holes such that the tips are received in the receiving features to restrict relative motion between the base member and the guide member; and
in the unlocked configuration, the locking posts are retracted such that the tips are withdrawn from the receiving features to enable relative motion between the base member and the guide member.

10. A tibial resection guide configured to facilitate resection of a tibia to prepare the tibia for attachment of a tibial prosthesis, the tibial resection guide comprising: an anchoring assembly that secures the tibial resection guide to the tibia; a base member; a positioning assembly extending between the anchoring assembly and the base member to adjustably position the base member proximate a tibial plateau of the tibia; and a guide member comprising a slot sized to receive a cutting blade configured to resect the tibial plateau; wherein the guide member is movably coupled to the base member such that the guide member is movable along an arcuate path, relative to the base member, around the tibial plateau, wherein the base member comprises two base member attachment features positioned proximate two opposing ends of the base member, wherein the positioning assembly is attachable to either of the base member attachment features.

11. The tibial resection guide of claim 10, wherein:
the base member comprises a base member attachment feature;
the guide member comprises a guide member attachment feature; and
the guide member attachment feature has a shape complementary to that of the base member attachment feature such that the guide member attachment feature and the base member attachment feature cooperate to slidably couple the guide member to the base member.

12. The tibial resection guide of claim 11, wherein:
one of the base member attachment feature and the guide member attachment feature comprises a dovetail-shaped protrusion extending along a first arcuate pathway;
the other of the base member attachment feature and the guide member attachment feature comprises a dovetail-shaped recess extending along a second arcuate pathway; and
the dovetail-shaped recess slidably receives the dovetail-shaped protrusion.

13. The tibial resection guide of claim 10, further comprising a locking member movably coupled to at least one of the base member and the guide member;
wherein:
the locking member is actuatable between a locked configuration and an unlocked configuration;
with the locking member in the locked configuration, the guide member is fixedly secured to the base member;
with the locking member in the unlocked configuration, the guide member is movable along the arcuate path, relative to the base member;
the locking member comprises a plurality of locking posts, each of which comprises a tip;
the base member comprises a plurality of locking holes, each of which receives one of the locking posts;
the guide member comprises a plurality of receiving features;
in the locked configuration, the locking posts extend fully through the locking holes such that the tips are received in the receiving features to restrict relative motion between the base member and the guide member; and
in the unlocked configuration, the locking posts are retracted such that the tips are withdrawn from the receiving features to enable relative motion between the base member and the guide member.

14. The tibial resection guide of claim 10, further comprising a locking member movably coupled to at least one of the base member and the guide member;
wherein:
the locking member is actuatable between a locked configuration and an unlocked configuration;
with the locking member in the locked configuration, the guide member is fixedly secured to the base member;
with the locking member in the unlocked configuration, the guide member is movable along the arcuate path, relative to the base member;
with the locking member in the unlocked configuration, the guide member is movable from a first position to a second position, relative to the base member;
the locking member is actuatable to the locked configuration with the guide member in the first position to lock the guide member in the first position; and
the locking member is also actuatable to the locked configuration with the guide member in the second position to lock the guide member in the second position.

15. The tibial resection guide of claim 14, wherein:
with the locking member in the unlocked configuration, the guide member is further movable to a third position, relative to the base member; and
the locking member is further actuatable to the locked configuration with the guide member in the third position to lock the guide member in the third position.

16. A tibial resection guide configured to facilitate resection of a tibia to prepare the tibia for attachment of a tibial prosthesis, the tibial resection guide comprising: an anchoring assembly that secures the tibial resection guide to the tibia; a base member; a positioning assembly extending between the anchoring assembly and the base member to adjustably position the base member proximate a tibial plateau of the tibia; and a guide member comprising a slot sized to receive a cutting blade configured to resect the tibial plateau; wherein the guide member is movably coupled to the base member such that the guide member is movable along an arcuate path, relative to the base member, around the tibial plateau, further comprising a locking member movably coupled to at least one of the base member and the guide member; wherein: the locking member is actuatable between a locked configuration and an unlocked configuration; with the locking member in the locked configuration, the guide member is fixedly secured to the base member; and with the locking member in the unlocked configuration, the guide member is movable along the arcuate path, relative to the base member, wherein: the locking member comprises a plurality of locking posts, each of which comprises a tip; the base member comprises a plurality of locking holes, each of which receives one of the locking posts; the guide member comprises a plurality of receiving features; in the locked configuration, the locking posts extend fully through the locking holes such that the tips are received in the receiving features to restrict relative motion between the base member and the guide member; and in the unlocked configuration, the locking posts are retracted such that the tips are withdrawn from the receiving features to enable relative motion between the base member and the guide member.

17. The tibial resection guide of claim 16, wherein:
the base member comprises a base member attachment feature;
the guide member comprises a guide member attachment feature; and
the guide member attachment feature has a shape complementary to that of the base member attachment feature such that the guide member attachment feature and the base member attachment feature cooperate to slidably couple the guide member to the base member.

18. The tibial resection guide of claim 17, wherein:
one of the base member attachment feature and the guide member attachment feature comprises a dovetail-shaped protrusion extending along a first arcuate pathway;
the other of the base member attachment feature and the guide member attachment feature comprises a dovetail-shaped recess extending along a second arcuate pathway; and
the dovetail-shaped recess slidably receives the dovetail-shaped protrusion.

19. The tibial resection guide of claim 16, wherein:
with the locking member in the unlocked configuration, the guide member is movable from a first position to a second position, relative to the base member;
the locking member is actuatable to the locked configuration with the guide member in the first position to lock the guide member in the first position; and
the locking member is also actuatable to the locked configuration with the guide member in the second position to lock the guide member in the second position.

20. The tibial resection guide of claim 19, wherein:
with the locking member in the unlocked configuration, the guide member is further movable to a third position, relative to the base member; and
the locking member is further actuatable to the locked configuration with the guide member in the third position to lock the guide member in the third position.

* * * * *